(12) United States Patent
Nelson et al.

(10) Patent No.: US 6,216,540 B1
(45) Date of Patent: *Apr. 17, 2001

(54) HIGH RESOLUTION DEVICE AND METHOD FOR IMAGING CONCEALED OBJECTS WITHIN AN OBSCURING MEDIUM

(76) Inventors: Robert S. Nelson, 2922 Upshur St., San Diego, CA (US) 92106; Reuven D. Zach, 1039 N. Harper Ave., #8, Los Angeles, CA (US) 90046

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/779,011

(22) Filed: Dec. 10, 1996

Related U.S. Application Data

(63) Continuation-in-part of application No. 08/480,760, filed on Jun. 6, 1995, now abandoned, and a continuation-in-part of application No. 08/597,447, filed on Feb. 2, 1996, now Pat. No. 5,999,836, which is a continuation-in-part of application No. 08/480,760, filed on Jun. 7, 1995.

(51) Int. Cl.⁷ .................................................. G01N 29/00
(52) U.S. Cl. .............................................................. 73/633
(58) Field of Search ............................ 73/596, 603, 607, 73/627, 632, 644, 633; 128/660.01, 660.04, 660.05, 660.07, 662.02, 662.03, 663.01

(56) References Cited

U.S. PATENT DOCUMENTS

| 4,296,753 | * | 10/1981 | Goudin ................................ 128/660 |
| 4,347,850 | * | 9/1982 | Kelly-Fry et al. .................... 128/660 |
| 4,429,577 | * | 2/1984 | Sorenson et al. ....................... 73/644 |
| 4,441,503 | * | 4/1984 | O'Donnell ............................ 128/660 |

(List continued on next page.)

OTHER PUBLICATIONS

"Experimental Examination of the Quantitative Imaging Properties of Optical Diffraction Tomography," T.C. Wedberg and J.J. Stamnes J. Opt. Soc. Am. A, vol. 12, No. 3/Mar. 1995, pp. 493–500.

(List continued on next page.)

Primary Examiner—Richard A. Moller
(74) Attorney, Agent, or Firm—Lyon & Lyon LLP

(57) ABSTRACT

A method and apparatus are provided for imaging and identifying concealed objects within an obscuring medium using radiation (optical, photo-acoustic, ionizing, and/or acoustic) optimized for imaging (e.g. temporal properties, spectral bandwidth, directionality, polarization, etc.). Radiation propagates through, interacts with, exits the medium and the object, and is detected/imaged. Image quality can be improved if radiation is collimated and/or if transmission and/or backscattered measurements from a number of perspectives are used to improved image reconstruction. Coupling materials can be employed during image acquisition to enhance radiation coupling as well as providing desirable absorption and scattering properties. Contrast materials and agents can also aid in the detection of concealed objects. Adaptive methods, e.g. using reference objects, including implementations based on the concept of guide stars, can improve the imaging process. The surface can be monitored and groomed to enhance the imaging process. Tomosynthesis techniques can be used to reconstruct images. Acousto-optic effects may be observed when both optical radiation and acoustic radiation are introduce into the medium. A laser vibrometry, speckle, or holographic interferometry imaging technique can be used to readout the acoustic waveform exiting the medium surface directly or after interacting with a deformable mirrored or reflective layer coupled to the medium. The medium may be prepared prior to imaging in order to reduce surface irregularities and roughness. Multi-layer mirrors and capillary optics can be used to enhance imaging systems which use ionizing radiation. Resistance images can be obtained using probes to penetrate the medium.

25 Claims, 12 Drawing Sheets

U.S. PATENT DOCUMENTS

| | | |
|---|---|---|
| 4,649,275 | 3/1987 | Nelson et al. . |
| 4,767,928 | 8/1988 | Nelson et al. . |
| 4,807,637 | 2/1989 | Bjorkholm . |
| 4,829,184 | 5/1989 | Nelson et al. . |
| 4,948,974 | 8/1990 | Nelson et al. . |
| 5,178,150 * | 1/1993 | Silverstein et al. ............. 128/662.06 |

OTHER PUBLICATIONS

"Special Issue: Time–Resolved Imaging & Diagnostics in Medicine," James G. Fujimoto Optics & Photonics News, Oct. 1993, vol. 4, No. 10.

"Remote Sensing of Seismic Vibrations by Laser Doppeler Interferometry," Albert J. Berni Geophysics, vol. 59, No. 12 (Dec., 1994) pp. 1856–1867.

"Focusing and Steering of Ultrasonic Waves Generated by a Sixteen Laser Source Array," MH Noroy, D Royer, and M Fink SPIE, vol. 1733 (1992) pp. 239.

"Wide–Band X–Ray Optics with a Large Angular Aperature," VA Arkad'ev, AI Kolomiitsev, MA Kumakhov, IY Ponomarev, IA Khodeev, UP Chertov, and IM Shakhparonov Sov. Phys. Usp. 32(3), Mar. 1989, pp. 271–276.

"On the Concentration, Focusing, and Collimation of X–Rays and Neutrons Using Microchannel Plates and Configurations of Holes," SW Wilkins, AW Stevenson, KA Nugent, H Chapman, and S Steenstrup Rev. Sci. Instrum. 60(6), Jun. 1989, pp. 1026–1036.

"Measurements on an X–Ray Light Pipe at 5.9 and 14.4 keV," WT Vetterling and RV Pound J. Opt. Soc. Am., vol. 66, No. 10, Oct. 1976, pp. 1048–1049.

"Transport of X–Rays Along Capillary X–Ray Waveguides Under Conditions of Total External Reflections from Curved Surfaces," VA Arkad'ev, VE Kovantsev, AI Kolomiitsev, MA Kumakhov, and IY Ponomarev Phys. Chem. Mech. Surfaces, 1990, vol. 6(1), pp. 82–91.

"Propagation and Scattering of Ultrasound in Random Media," E Soczkiewicz Acoustooptics and Applications World Applications World Scientific, 1990, pp. 395–400.

"Acoustooptical Detection in Photocoustical Experiments," A. Sliwinski Acoustooptics and Applications, World Scientific, 1990, pp. 263–278.

"Laser Doppler and Time–Varying Speckle: A Reconciliation," J.D. Briers J. Opt. Soc. Am. A, vol. 13, No. 2, Feb. 1996, pp. 345–350.

"Infrared Imaging of Buried Objects by Thermal Step–Function Excitations," P. Li, A Maad, F Moshary, MF Arend, and S Ahmed Applied Optics, vol. 34, No. 25, Sep. 1, 1995, pp. 5809–5816.

"Applications of Photoacoustic Sensing Techniques," AC Tam Reviews of Modern Physics, vol. 58, No. 2, Apr. 1986, pp. 381–431.

"Random Modulation CW Lidar Using New Random Sequence," C Nagasawa, M Abo, H Yamamoto, and O Uchino Applied Optics, vol. 29, No. 10, Apr. 1, 1990, pp. 1466–1470.

"Generalized Tomosynthesis for Focusing on an Arbitrary Surface," J Liu, D Nishimura, and A Macovski IEEE Transactions on Medical Imaging, vol. 8, No. 2, Jun. 1989, pp. 168–172.

"Object Detection and Imgaing with Acoustic Time Reversal Mirrors," M Fink SPIE Fol. 1942, pp. 256–267.

* cited by examiner-

HIGH RESOLUTION DEVICE AND METHOD FOR IMAGING CONCEALED OBJECTS WITHIN AN OBSCURING MEDIUM

RELATED APPLICATION INFORMATION

This application is a continuation in part to U.S. patent application Ser. No. 08/480,760, filed Jun. 6, 1995, now abandoned and a continuation in part to U.S. patent application Ser. No. 08/597,447, U.S. Pat. No. 5,999,836, filed Feb. 2, 1996, which is a continuation-in-part to above-described U.S. patent application Ser. No. 08/480,760, filed Jun. 7, 1995 the disclosures of which are hereby incorporated by reference as if fully set forth herein.

FIELD OF THE INVENTION

The present invention relates to the location and identification of concealed (buried, hidden, or shielded from view) objects in an obscuring (scattering, absorbing, distorting) medium using acoustic, optical, and ionizing radiation devices and methods.

BACKGROUND OF THE INVENTION

The present invention can be understood by considering the limitations of techniques currently employed in locating and identifying concealed objects such as mines, ordnance, weapons, machinery, pipes, cables, tunnels, barrels, hazardous chemicals and pollutants, illicit materials, pests, biological disorders and anomalies, etc., when such concealed objects are located within an obscuring medium (i.e. a medium which is capable of scattering and absorbing radiation and/or distorting the propagation of radiation through variations or inhomogeneities in the local refractive index).

Variations in the refractive index of a medium are encountered in fields such as astronomy (ground based telescopes peering through atmospheric refractive turbulence (which has led to the development of an artificial laser-based guide star, a particular kind of reference object which approximates a point source of radiation)), geology (stratified layers of soil or sea bottom, pools of gas, oil, water, etc.), and medical imaging (ultrasound, optical, microwave). Implementations of this invention are preferably used with obscuring mediums such as snow and ice, gravel, sand, soil, mud, river bottom, lake bottom, ocean bottom, biological waste, sewage or sludge, and human tissue.

The obscuring medium may simply be referred to as the medium. See, Underground and Obscure Object Imaging and Detection, SPIE vol. 1942 (N. Del Grande, et. al., eds. 1993); and Aerial Surveillance Sensing Including Obscured and Underground Object Detection, SPIE vol. 2217 (I. Cindrich, et. al., eds., 1994). In the case of buried mines, chemical or biological sensors (typically sniffer dogs, laser spectroscopy, mass spectroscopy, etc.) have been used with limited success. A number of imaging techniques have been implemented which employ acoustics (seismic studies), ionizing radiation (primarily gamma rays, x-rays, neutrons, and to a lesser extent charged particles), low-energy electromagnetic radiation (mainly covering UV, visible, infrared, microwave, and radar), magnetic fields (such as gradiometers), thermal radiation, etc. Low-energy electromagnetic radiation will be referred to as electromagnetic or optical radiation. Neutrons need not interact with materials solely through ionization to result in radiation (or byproducts) which can be detected. Neutron radiation used in this manner will still be included in the group referred to as ionizing radiation.

Current technologies that employ ionizing radiation may be unacceptable in some circumstances because they may require some type of accelerator (including x-ray tubes) with a heavily filtered output or an intense radioisotope source (since the source itself is self-attenuating, does not produce a directional beam, and radiation of a narrow bandwidth is desirable), and energy-sensitive receivers. In addition, current technologies require significant shielding. Technologies that employ x-ray tubes may suffer from very high power consumption, requiring specialized tubes or instead resulting in a reduction in operational lifetime. It will be shown that our invention will overcome the limitations of these old technologies by filtering and focusing ionizing radiation in order to increase beam intensity, improve beam directional and spectral properties, and/or enlarge the acceptable beam cross section which will, in turn, enable radioisotopes, x-ray tubes, neutron generators, neutron-emitting isotopes, etc., ionizing radiation sources for imaging objects within an obscuring medium.

A number of factors will limit the practical implementation of an imaging technique or system. Scattering, absorbing, and distorting properties of the obscuring medium and object materials typically impose limitations on the waveform and type of radiation. Coupling inefficiencies or losses can result from source and receiver limitations and interfere with the goal of delivering useful radiation from the source to the medium and collecting useful radiation exiting the medium. Additional inefficiencies or losses can result from radiation propagation problems experienced at the interfaces between mediums containing the source, receiver, and object due to discontinuities. Two other conditions, if present, will further degrade current imaging techniques: the presence of additional objects (in addition to any nonuniformity in the local refractive index) and a nonuniform interface (an irregular or rough surface) between the obscuring medium and the mediums containing the source and receiver. For example, an obscuring medium such as the ground can contain stones, roots, voids, etc., and vary in soil composition, moisture content, gases, biology, etc. The surface of the ground can be broken, rough, sloped, etc. These two conditions also complicate optical imaging in tissue such as breast tissue. The viability of a particular imaging technique can be increased if at least some of the effects of coupling inefficiency, a nonuniform surface, and an inhomogeneous medium can be reduced.

Adequate levels of (useful) radiation need to be coupled (focused and directed) efficiently from the source to the region of interest and from the region of interest to a detector. Discontinuities which result from physical properties of the mediums containing the source, concealed object, and detector as well as rough or irregular interfaces must be considered. In some cases external structures such as ground cover (vegetation, etc.) or the effects of wind, temperature, noise (man-made, etc.), and other environmental conditions can introduce additional levels of complexity. Furthermore, the concealed object, such as a land mine, often represents a hazard and is designed and placed to avoid detection via a particular technology. For example, non-magnetic land mines are widely used and many mines are of a shape and size that they are not easily detected using ground-penetrating radar.

The probability of detecting the concealed object can be improved by examining those aspects of the particular problem which we can reasonably hope to influence. The approach taken here is largely based on previous work by the present inventors, Nelson et. al., for medical imaging and specific non-destructive testing problems. See U.S. Pat. No.

4,937,453 (Jun. 26, 1990), U.S. Pat. No. 5,017,782 (Nov. 19, 1990), U.S. Pat. No. 4,958,368 (Sep. 18, 1990), U.S. Pat. No. 4,969,175 (Nov. 6, 1990), U.S. Pat. No. 4,649,275 (Mar. 10, 1987), U.S. Pat. No. 4,767,928 (Aug. 30, 1988), U.S. Pat. No. 4,829,184 (May 9, 1989), U.S. Pat. No. 4,948,974 (Aug. 14, 1990), U.S. patent application Ser. No. 08/480, 760, filed Jun. 6, 1995, and U.S. patent application Ser. No. 08/597,447, filed Feb. 2, 1996, the disclosures of which are hereby incorporated by reference as if fully set forth herein. These earlier works describe not only a number of data acquisition and noise correction techniques, but also the advantages of creating an efficient imaging environment with predictable properties.

The identification and classification problems that the present invention addresses require improvements and new additions to the present state of the art. In addition, the various environments (sand, mud, snow, dirt, flooded fields, rough terrain, ground cover, ocean bottom, river bottom, lake bottom, etc.) in which specific implementations of the invention can be utilized imply that requirements such as survivability, low cost, and maintainability should be considered in the design of imaging systems for use in these environments. Survivability problems will be of reduced importance for implementations of the invention which may be employed in other environments (medical, non-destructive testing, etc.).

The ability of an imaging system to locate and identify a concealed object in an obscuring medium can be improved by incorporating enhancements which would: (1) optimize source/receiver parameters, source utilization, and the use of appropriate data acquisition and signal processing techniques and algorithms; (2) optimize radiation transport into, through, and out of the medium; and (3) exploit or modify properties of the object and medium.

Optimizing source/receiver parameters, source utilization, and the use of appropriate data acquisition and signal processing techniques and algorithms, may also involve a mix of imaging technologies (for example, optical and acoustic) and timely acquisition rates. High resolution imaging techniques might be very time consuming in comparison to techniques which are adequate for identifying the presence of potential objects of interest. In addition, the cost of a large area, high resolution detection system may be substantial relative to a small area, high resolution detection system. In many situations it may be more cost-effective to use adequate imaging resolution to detect the presence of potential objects of interest and then use high resolution imaging techniques to help identify the object. Searching a large area using a high resolution imaging method may simply be too time consuming, particularly if the density of potential objects is low.

The radiation field entering and leaving the obscuring medium can be severely modified by scattering, absorbing, and refractive effects. The surface of an obscuring medium such as soil is typically rough and irregular. Vegetation may also cover at least part of the surface. The volume of this medium is likely to be inhomogeneous. Non-invasive detection systems currently in use for applications such as buried mine detection (for example, radar) typically suffer from the radiation transport problems listed. Radiation transport problems may also reduce the incentives to acquire a more complete data set. Often only a single view of the medium is acquired (or at least the range of views is quite limited). Enhancing radiation transport into, through, and out of an obscuring medium such as soil may involve modifying the obscuring medium, its surface, or both. In addition, the likelihood of detecting a concealed object may be further improved by modifying the concealed object or its immediate environment.

New non-invasive and invasive devices and/or modes of imaging an object concealed in an obscuring medium using ionizing radiation, optical, acousto-optical, acoustic (including photo-acoustic) and/or mechanical imaging techniques are needed to improve image quality (including material characterization accuracy). Particular problems which need to be addressed are the need for improved radiation coupling into and out of the scattering medium as well as improved transmission through the medium, the need to enhance the information content of detected radiation (which can involve modifying the object and the medium), and the need to acquire a data set which is more complete (which frequently involves sampling the medium from more than one direction (multiple projections), more than one wavelength or energy, more than one waveform, etc.).

It is desirable to exploit various physical properties of the object and the medium such as reflectivity, scattering, absorption, frequency-dependence, polarization-dependence, material composition, density, internal and external structure, impedance, permitivity, conductivity, emissivity, inductance, dielectric constant, bulk modulus, radiation velocity, radiation cross section, characteristic radiation, resistance to penetration, etc. It is desirable to implement methods utilizing improvements such as increased source coupling efficiency (source utilization efficiency) to the region of interest and a radiation beam with well defined properties (angular distribution, energy distribution, polarization, pulse width, modulation frequency, etc.) to enhance imaging of a concealed object in an obscuring medium when ionizing radiation is employed. For example, it would be desirable to have methods using thermal energy or an acoustic field to modify the properties of a localized volume of the obscuring medium for optical radiation (under the appropriate conditions) also exploited for ionizing radiation.

However, prior devices and methods do not address these concerns.

SUMMARY OF THE INVENTION

The present inventions are apparatuses and methods which address the problems of locating and identifying (imaging) concealed objects in an obscuring medium. One or more of the physical properties of the object and the medium (such as reflectivity, scattering, absorption, frequency-dependence, polarization-dependence, material composition, density, internal and external structure, impedance, permitivity, conductivity, emissivity, inductance, dielectric constant, bulk modulus, radiation velocity, radiation cross section, characteristic radiation, etc.) can be exploited in order to image the object in the obscuring medium. Modifications to the obscuring medium or the object itself can be used to enhance location or identification of the object. Detection and identification problems are addressed through the use of various types of radiation (electromagnetic, acoustic (including photo-acoustic), ionizing, etc.) sources and receivers (contact and non-contact), various radiation waveforms, radiation coupling materials (liquids, such as water, and gels with appropriate indices of refraction, absorption and scattering attenuation coefficients, etc.), the use of single or multiple angled beams (in which the range of angles typically includes normal incidence), the use of virtual radiation beams, the use of various collimation techniques, and the use of contact sensors (including probes). In some cases effects such as the use of the Brewster angle can be exploited.

Many of these concepts were disclosed in prior applications by the present inventors, Nelson, et. al., in which the obscuring medium was human tissue or a container. See, U.S. patent application Ser. No. 08/480,760, filed Jun. 6, 1995; and U.S. patent application Ser. No. 08/597,447, filed Feb. 2, 1996; both of which were incorporated by reference above, and which detail imaging systems which include transmission, backscatter, and combined transmission/backscatter imaging formats. Thus, for an object (man-made or otherwise) concealed in an obscuring medium, previously disclosed techniques can be utilized and enhanced, and new techniques can be introduced.

A number of aspects to the problem of imaging a concealed object in an obscuring medium need to be examined in order to improve the probability of successful detection. For example, with a remote source and receiver, radiation losses at the entrance and exit interfaces of the obscuring medium can severely limit the effectiveness of the imaging system. Enhancing radiation transport into, through, and out of an obscuring medium may involve modifying the obscuring medium, its surface, or both. These modifications can include brushing, smoothing (buffing), applying a suitable coating to the surface in order to reduce surface roughness and irregularities, and minimizing air gaps. Coupling materials can be used when appropriate. For example, in the case of acoustic imaging a (non-contact) photo-acoustic source (that is, a source that produces acoustic radiation due to a photo-acoustic effect) can be used to generate an acoustic waveform at or below the surface of the medium. A photo-acoustic source can be utilized as a non-contact source of acoustic radiation. An imaging module may also be employed to improve radiation coupling and provide a controlled environment for use with contact and non-contact sources.

Exploiting or modifying properties of the concealed object and obscuring medium is another way to enhance an imaging system. Fluids such as water, in addition to their use as coupling materials or surface smoothing materials, can function as contrast materials due to their own physical properties. Such fluids can also serve as delivery materials (delivery systems) for agents such as gases, chemicals, biological organisms, radioisotopes, etc. that will preferentially avoid or seek out or be deposited on (or next to) the object and improve the probability of detection and/or attack the integrity of the object. Thus, a fluid such a water can function as a contrast material or a delivery system for agents (indeed, the fluid itself can be the agent) independently from its use as a coupling material. A coupling material can also function as an agent.

The concepts of contrast materials, agents, and delivery systems is well-known in the field of medicine. The agent can target or interact with the concealed object or the obscuring medium. This can alter the object or medium in some manner (for example, the agent can deliver thermal energy to the object or the medium or initiate a reaction which results in enhanced detectivity). An agent might effect the shape or surface properties of the object. The degree of interaction of an object or the local medium with a contrast material or agent can be important. An object may not be porous, preventing the dispersion of the contrast material and thus causing the contrast material to accumulate (or pool) at some region on or near its surface (such as a ridge, the front or rear, etc.). Alternately, the object may be porous and may preferentially absorb an agent or contrast material relative to the behavior of the surrounding medium. The obscured object may alter the surrounding medium resulting in compaction or voids where a contrast material might accumulate. Indeed, the presence of high clutter levels or a changing noise pattern after the introduction of a contrast material may indicate that the local medium was disturbed by the burial of an object.

Externally induced changes in the temperature of, or fields present in, the concealed object (through induction or heating from external radiation) are possible. In some cases a fluid can aid in the delivery (or removal) of thermal energy to (or from) the object. A fluid can be heated or cooled prior to or after interacting with the medium. The actions of the contrast material or agent can be activated or accelerated through the use of an external radiation source. The probability of detection can be improved by altering the environment in the vicinity of the object (such as altering the medium or modified medium locally by manipulating parameters such as density or composition). For example, a material such as water can permeate the soil surrounding a concealed object and thus improve the uniformity of the medium surrounding the object.

Another example involves initiating a reaction within the obscuring medium which generates gas which can increase the acoustic (or optical) concealed object cross section (or the presence of the gas itself might be detected). Energy can be coupled into the object which can then be detected by re-radiation, a resonant condition, or energy conversion (often heat) providing a useful imaging signature.

Yet another technique is to image an area, induce the concealed object (or obscuring medium) to shift its position, and then re-image that same area. A comparison of the "before" and "after" images may indicate a change which provides information which would be difficult to detect based on a single image (for example, a change in the background noise pattern or speckle pattern, the obscuring of return signals from other objects, etc.). In the case of a medium such as soil, a vibrating driver or pounding device can be used to shake or jiggle the soil in a region contained or bounded by a perimeter wall. In some cases this can have the added benefit of causing the object (such as a mine or piece of ordnance) to move closer to the surface.

Another approach (invasive, involving direct contact) to concealed object detection is to penetrate the obscuring medium using rod-like probes, each connected to its own pressure sensor. An array of probes can be comprised of smaller arrays (sub-arrays). Probes would penetrate the obscuring medium either up to a pre-defined maximum depth or until a maximum resistance level (which, if the medium is ground, river bottom, ocean bottom, etc. can be soil or marine sediment specific) was reached. Thus, a directional, pressure-dependent outline of objects whose resistance exceeds some level can be obtained. Since the resistance encountered by each probe can be monitored and recorded, a three-dimensional resistance map of the medium can be obtained. Also, an array or sub-array of probes can be rotated and/or translated within the plane of the array as well as rotated (tilted) with respect to the previous sampling direction. Thus, the medium (and objects within the medium) can be examined from multiple views which are not limited to a single plane. Probes can also interact with the object. Other specialized probes can also be used for data acquisition or as delivery systems. Probes can be rod like, curved, or flexible depending on the requirements of the imaging task.

Techniques developed in the fields of medical imaging, treatment, and therapy (including radiation therapy), optical imaging, microwave and radar imaging, acoustics, non-destructive testing and evaluation, communications, and geophysics can be applied to this problem. For example, non-contact acoustic readout at the surface of the medium can be achieved using optical speckle or holographic interferometry, point and area scan laser time-of-flight (TOF), optical TOF holography, laser Doppler interferometry, or differential laser Doppler interferometry methods. See, A. Berni, Remote Sensing of Seismics Vibrations by Laser Doppler Interferometry, Geophysics vol. 59, no. 12, pp. 1856–1867 (1994). A non-contact acoustic input method involves generating an acoustic waveform at or below the surface of the medium by exploiting the photo-acoustic effect due to (typically) a laser beam incident on the surface. See M. Noroy, et. al., Focusing and Steering of Ultrasonic Waves Generated by a Sixteen Laser Source Array, 1733 SPIE 239–248 (1992); A. Tam, Applications of Photo-acoustic Sensing Techniques, 58/2 Rev. Mod. Physics 381–431 (1986); A. Sliwinski, Acousto-optical Detection in Photo-acoustic Experiments, in Acousto-optics and Applications 263–278 (A. Sliwinski, et. al., eds. 1990).

Acoustic and electromagnetic (optical) time-resolved (such as Time of Flight (TOF)), continuous wave, diffusive wave, and encoded wave techniques have been utilized to enhance imaging in highly scattering and absorbing media. See, Medical Optical Tomography, SPIE vol. IS11 (G. Muller, et. al, eds. 1993); Optics & Photonics News, Vol. 4, No. 10, pp. 9–32 (J. Fujimoto, ed. 1993); E. Soczkiewicz, Propagation and Scattering of Ultrasound in Random Media, in Acousto-optics and Applications 395–400 (A. Sliwinski, et. al., eds. 1990); and A. Ishimaru, Wave Propagation and Scattering in Random Media, Volumes 1, 2 (Academic Press 1978). Photon diffusive wave imaging (and spectroscopy) techniques (also referred to as frequency domain or photon migration or photon diffusive wave techniques) can represent an alternative to time-resolved optical methods. Amplitude and phase modulation (and even phase encoding) have been utilized for composition and location identification. Photon diffusive wave tomography imaging has been reported and acoustic diffusive wave imaging can be implemented.

Properties such as the coherence, polarization, spectral content, and directional nature (angular distribution) of the appropriate radiation field can be exploited. Source and receiver collimation can also be used to reduce the effects of degrading scattered radiation or at least limit the sampling area (the field of view) to a specific region. Forms of collimation might include the use of lenses, mechanical apertures (slits, slots, holes), heterodyning or homodyning techniques, gating (a time-resolved aperture), gaps (such as air or gas-filled gaps or gaps filled with coupling material), directionally-sensitive and spectrally sensitive (narrow bandwidth) filters such as multilayer mirrors and interferometers, masks, coded or patterned apertures, fibers, wave guides, phased arrays (sometimes referred to as focused arrays or beam forming arrays), electronic collimation, coupling materials, reciprocating collimators, etc.

Multiple sources and receivers (including multiple angle projections) can be used to synthesize an image from multiple projections. Standard image reconstruction techniques include beam forming, Fourier-synthesis holography, tomosynthesis, finite element reconstruction techniques, and computed tomography (CT). See, e.g., A. Kak, et al., Principles of Computerized Tomographic Imaging (1988); Image Recovery Theory and Application (H. Stark ed. 1987); and J. Liu, et al., IEEE Trans Medical Imaging, Vol.8, No. 2, pp. 168–172 (1989). Typical signal processing techniques used to enhance data include deconvolution, matched filter (including matched field filter) and adaptive methods. See, G. Kino, Acoustic Waves: Devices, Imaging, and Analog Signal Processing (1987). It can be useful for applications where the surface of the medium or a module coupled to the medium is read out optically (or where a coupling material, contrast material, or agent delivery material will be added to the medium) to acquire one or more reference images (typically prior to image acquisition). These reference images can be used to compensate for or estimate the signal contribution from the surface and/or interior of the medium. A reference image of the readout surface can also be used with interferometric techniques. In some cases the reference image(s) can simply be a composite which is representative of a larger region which is to be scanned. Acoustic reference images can also be acquired. (Indeed, this concept can be extended to include ionizing radiation reference images.) A reference image(s) can be compared with newly acquired images to reveal differences which might indicate the presence of an object. A data base of reference images or signal patterns can be established so that the identification process can be aided using pattern matching techniques. An extension of the idea of a reference image involves the use of a reference object (for example, a guide star).

Radiation scattered in the appropriate direction can be treated as if it were a virtual collimated beam. This virtual beam appears to originate from within the medium rather than at the surface of the medium as is the case for an externally incident beam. The manner in which optical radiation interacts with a medium can be altered by the presence of an acoustic field (the acousto-optic effect). Changes in the local optical properties of the obscuring medium can be measured by intersecting an acoustic field with an optical radiation field. Thus, three-dimensional imaging is possible using one radiation field to modify another. The concept of using an acoustic radiation field to modify at least a localized volume of the medium can be extended such that heating is used to modify at least a localized volume within the medium. It is also possible to observe effects such as the interference between two or more acoustic or optical (or ionizing) radiation fields (focused radiation fields) and how this interference depends upon location and local properties (as well as the paths followed by the radiation fields prior to interfering). Many of the concepts mentioned above are described in detail by the present inventors, Nelson, et. al., in U.S. patent application Ser. No. 08/480,760, filed Jun. 6, 1995, and/or U.S. patent application Ser. No. 08/597,447, filed Feb. 2, 1996, the disclosures of which are hereby incorporated by reference as if fully set forth herein.

Intense focused acoustic fields can be used not only for imaging purposes, but also to temporarily or permanently modify the properties of the obscuring medium or the concealed object. The use of intense focused acoustic fields is exploited in standard lithotripsy, where convergent acoustic fields pulverize kidney stones. Monitoring lithotripsy treatment typically involves using ionizing electromagnetic radiation (x-rays). Lithotripsy differs from the use of acousto-optic interactions for imaging in that modifications to the properties of the object (or surrounding medium) are intended to be permanent with lithotripsy.

The problem of detecting a concealed object in an obscuring medium (for example, a soil which is a composite of many materials) is in many ways similar to detecting objects embedded in human tissue such as the breast using ionizing, and in particular, low-energy radiation. Both mediums can be distorting, are absorptive, and are highly scattering for acoustic, electromagnetic (optical), and (in some cases) ionizing radiation of interest, may have irregular or rough surfaces, and have index of refraction mismatches with air which can result in inefficient coupling of acoustic and optical radiation into and out of the medium. The present inventors, Nelson et. al., teach methods to compensate for these problems when imaging tissue with low-energy radiation as well as various imaging techniques e.g., the concepts of using an optical coupling material (fluid or gel) to reduce scattering and reflection losses at the air-skin interface and modifying (or compensating for) the nonuniform breast surface have been introduced previously). See, U.S. patent application Ser. No. 08/480,760, filed Jun. 6, 1995.

Additional options are available for imaging a non-human (i.e. non-biological) subject since there are fewer restrictions on the radiation levels that can be employed and on how the medium (or object) can be modified (at least temporarily). Thus, radiation can be introduced into the medium and various effects (such as resonance and re-radiation, including conversion to another energy form or another frequency) can be observed which might prove unacceptable in medical imaging due to patient risk. This approach has a parallel in biomedical optics when fluorescence or Raman scattering are observed in illuminated tissue. In certain medical applications temporary, limited modifications of the tissue medium properties are acceptable. For example, introducing a contrast material (which are used in x-ray radiology, MRI, ultrasound, and nuclear medicine) into the object being imaged such as a vein, artery, or organ, introducing a gas into the lungs, introducing a biological agent which preferentially tags (interacts with) objects of interest, altering local tissue properties by heating or cooling, or using photo-acoustic effects to generate an acoustic pulse from within a small volume of tissue.

The present invention comprises apparatuses and methods directed to enhancing the imaging of an object in an obscuring medium. For imaging techniques which use acoustic and/or optical radiation, specialized source and receiver devices and radiation coupling materials (e.g., fluids such as water) can be used to ensure efficient coupling of a (preferably) collimated radiation beam (from a laser, waveguide, phased array, transducer or photo-acoustic source, etc.) into, through, and out of the obscuring medium. A beam or a number of beams (preferably) of relatively small spatial dimensions are used to obtain information regarding properties and images of an obscured object with high spatial resolution. Externally generated beams or internally generated "virtual" beams can interrogate the medium and object from multiple angles. Multiple two-dimensional images can be acquired for transmission (for example, if the medium is the ground and the source and/or receiver are within the medium or inside a pipe, tunnel, cave, etc.) and backscatter angled and virtual (preferably) collimated beams. Three-dimensional image information can be synthesized from the multiple angled collimated beams data, the multiple virtual collimated beams data, or an appropriate combination of the two sets of data. The use of multiple angled and virtual collimated beams can enhance the capability of an imaging system to recognized an object from a characteristic signal pattern or signature (which can be due to a resonance condition, fluorescence, re-radiation, a radiation pattern which is the result of its physical structure, its material composition, Doppler effects, etc.) as well as its (and its immediate surroundings) reflection, scattering, and absorption properties. Resonance signatures are affected by material properties of the components which comprise the object, their size and shape, and the surrounding environment. Effects such as external skin currents, the decay of eddy currents, cavity resonances, and their signal characteristics are well known. Diffusive wave tomography imaging can also be implemented.

The radiation source requirements (for optic, acoustic (including photo-acoustic), and acousto-optic imaging) can range from a continuous (i.e., continuous wave or CW) to a rapidly pulsed source. If the source produces a beam with a sufficiently short pulse (or coherence length), appropriate for time-resolved techniques such as Time of Flight (TOF), then the beam can be relatively small in at least one spatial dimension. It can be desirable to control the radiation source with a small aperture or focusing element, in which case a pulsed beam can be relatively small in three spatial dimensions instead of two spatial dimensions (typically regarded as the beam cross section normal to the beam axis). The rate at which a source is pulsed should preferably be rapid enough to ensure that an adequate integrated signal is detected before sources of environmental noise (temperature, motion, wind, etc.) become problematic. Additional properties of the source radiation field or fields which might be exploited include being frequency-tuneable, its spectral content (for example, a narrow bandwidth spectrum, the use of multiple narrow bandwidth spectra, a broad bandwidth spectrum, etc.), coherence, polarization, its directional properties (angular distribution), having a CW-modulated, coded or complex waveform, etc. A CW-modulated radiation source can also be used in diffusive wave imaging. A broad bandwidth spectrum might be advantageous when trying to detect resonance effects.

Source and receiver collimation can also be used to reduce the effects of degrading scattered radiation or at least limit the sampling area (the field of view) to a specific region. A number of collimation techniques are available for acoustics and optics including lenses, mechanical apertures (slits, slots, holes), gaps, time-resolved methods (heterodyning or homodyning techniques, various holographic techniques such as gating, short-coherence, Fourier-synthesis, quasi-Fourier synthesis, TOF gating, etc.), directionally-sensitive or spectrally-sensitive filters, directionally-sensitive and spectrally-sensitive filters such as multilayer mirrors and interferometers, polarization filters, masks, coded or patterned apertures, fibers, wave guides, phased arrays, electronic collimation, holography, reciprocating collimators, coupling materials, etc.

Multiple radiation types can be employed concurrently and may interact with each other (for example, acoustic radiation and optical radiation may interact via the acousto-optical effect). Interference effects such as the interference between two or more similar acoustic or optical (typically phase-modulated) radiation fields (focused radiation fields) can be measured and how the interference depends upon location and changes in the local properties of the medium (which may be due to the presence of an object). The paths followed by the radiation fields prior to interfering also need to be considered. For example, when the obscuring medium is breast tissue, it is preferable that compression devices (such as compression plates, preferably contoured) be employed since compression will significantly reduce the thickness of the volume which needs to be scanned (and, therefore, the maximum depth at which interference needs to be achieved) and provides for uniform radiation entrance and exit surfaces. The result of conversion of radiation from one type to another can also be imaged.

As was mentioned earlier, it is highly desirable to efficiently couple radiation into, through (if possible), and out of the obscuring medium. If the medium is the ground, it may be desirable to clear obstructions, such as ground cover, and reduce the effects of surface roughness and irregularities. Surface roughness and irregularities can be evaluated optically or acoustically in order to determine the need for corrective action. These optical (which can be passive or active, and can exploit polarization effects) and/or acoustic surface imaging systems (using air coupling in a non-contact imaging format) can also be used to locate objects such as surface mines or mines that are only partially obscured prior to scanning the medium. Surface roughness and irregularities can be diminished by traditional means (such as rakes) or by smoothing the surface using a rotating brush (similar in concept to a floor buffer) or applying a coating or additional layer that reduces the apparent roughness and irregularities (for example, spraying a layer of water over the surface). In cases such as buried mines, the mine is either not sensitive enough to be set off by the brush or the brush provides such a small cross section to a blast that it will suffer little or no damage (or the brush mechanism is inexpensive and easily replaced). In the case of surface mines the brush can be designed to disable the mine or clear it from the path. A blower or air jet (or water jet) can be included with surface imaging system and/or the rotating brush in order to clear debris (including surface mines) from the surface (as well as providing a non-contact mechanism for uncovering objects such as mines).

Once a concealed object such as a mine, ordnance, etc. is located, a number of techniques can be used to remove and disable it. It would be desirable to minimize human intervention at this point. Since the mine is likely to be near the surface, one inexpensive solution is to use a retrievable, arrow-like bolt attached to a cable. The tip of the bolt can be optimized to penetrate or incapacitate the mine, ordnance, etc. The bolt would be launched (using a suitable propellant, spring, etc.) into the soil and pierce the mine. If the mine does not explode while retracting the cable, it can then be rendered inoperable (if it is not yet incapacitated). An alternative implementation is to mechanically drive (or drill) the bolt into the medium and the object. The simple bolt design can be extended so that the bolt can provide additional functionality. For example, the arrow-like bolt can be easily modified so that it can also function as an electromagnet. This can aid in the retrieval of metal mines or ordnance (which may be located at greater depths). If a nearby object is attracted to the electromagnet bolt, then the increased resistance measured while retracting the bolt may indicate that an object is present. The bolt can also be modified (for example, it can be hollow and provide orifices or windows) to deliver an electric current, heat energy (or remove heat energy), a coolant, liquids (including liquids which have been heated or cooled), gases, chemicals, biological organisms, optical radiation, acoustic radiation, intense optical or acoustic radiation which may be sufficient to heat, melt, or vaporize materials, ionizing radiation, etc. which can aid in incapacitating the mine or ordnance or in establishing their presence. These modifications to the basic bolt design may require that tubes, wires, and fiber optics be attached to (or incorporated into) the bolt in addition to the cable. A bolt can also be modified to act as a retrieval system, using appropriate orifices and sensors to make radiation measurements and acquire samples (gases, chemicals, etc.). Use of the bolt can be implemented remotely and the components should demonstrate a high degree of survivability or are easily replaced. It will be shown that the concept of a (ground-penetrating/contact, destructive) bolt can be enhanced so as to permit contact imaging (using probes).

The present invention can also utilize a radiation coupling material, for example a liquid, such as water, to improve radiation coupling between a source (or source module) and/or receiver (or receiver module) and the surface (and the interior) of the obscuring medium. The coupling material can favorably modify (at least temporarily) the medium such that it appears to be more homogenous with the coupling material present. The coupling material can also aid in the transport of thermal energy to and from the volume being targeted and function as a lubricant for components that might slide over the surface of the ground (or medium being examined). A radiation coupling material (with appropriate index of refraction and/or scattering and absorption properties) can also be used to minimize discrepancies in the path length differences due to surface roughness and an irregular or slanted surface over a region of interest. This is particularly important for techniques which utilize phase or temporal properties of the radiation field, such as pulsed radiation which is evaluated by utilizing TOF analysis. Radiation coupling materials can be selected based upon their optical or acoustic (including photo-acoustic) properties. A coupling material with appropriate absorption characteristics can provide scatter reduction of radiation which travels a longer total path through the coupling material. If radiation attenuation by the coupling material is too severe then imaging must be completed before the coupling material permeates the medium. Providing a relatively uniform input and/or readout surface and enhancing the radiation transport properties of the medium should be beneficial whether or not the source or receiver are in contact with the medium.

A liquid (which can also function as a coupling material) can be used to deliver (or act as) a contrast material or it can be used as an agent delivery system. Contrast materials and agents such as gases, chemicals, radioisotopes, or biological organisms can be used to enhance the detectability of the concealed object (for example, by depositing the contrast material on or near the object or the result of the agent reacting with the object). The coupling material may itself be an agent material. Certain agent materials might be activated remotely. Agent activation can result from a variety of mechanisms such as photo-induced activation, temperature-induced activation, the disassociation into components, chemical induced activation, etc. For example, microwave or acoustic radiation can cause the temperature of the agent (e.g., water) to increase and heat the concealed object. Contrast materials and/or agents may be introduced into the obscuring medium prior to the start of data acquisition.

If sufficient energy is available, the agent can disassociate (or a material in the agent can start a reaction) and form bubbles which can enhance object contrast by their presence or absence. Collapsing bubbles (or the absence thereof) can also act as internal acoustic sources and so provide an additional imaging mechanism. The use of contrast materials and agent materials is well known in many fields including medical imaging (angiography, nuclear medicine, MRI, ultrasound), therapy (magnetic particles for tumor heating, photodynamic therapy), chemotherapy, and genetic therapy. The motion of the coupling material itself (or a contrast material or an agent material) can be tracked through the medium, providing information about the medium and objects in the flow path.

Another approach to enhancing detection is to redistribute the concealed object and/or the obscuring medium. The procedure involves first imaging a specific area, next inducing the object (or the medium) to shift its position, and then re-imaging that same area. A comparison of the "before" and "after" images may indicate a change which would be difficult to detect based on a single image (for example, a change in the background noise pattern or speckle pattern, the obscuring of return signals from other objects, etc.). In the case of a medium such as soil, a vibrating driver or pounding device can be used to shake or jiggle the soil. In some cases this can have the added benefit of causing the object (such as a mine or piece of ordnance) to move closer to the surface. It can be beneficial to surround the area which is to be jiggled or shaken with a partially buried frame. The walls of the frame will help constrain the motion of the soil. Shaking or jiggling the soil may also result in the detonation of an explosive object, which may or may not be considered desirable.

Yet another (contact) technique is to penetrate the obscuring medium using an array of rod-like probes (an enhancement to the bolt design described earlier), each connected to its own pressure sensor (see FIG. 10). The spacing of probes within the array would provide appropriate sampling (or sub-sampling) densities. A probe array can be assembled from smaller probe arrays (sub-arrays) which can function independently if desired. A driving force and/or a drilling action would cause the probes to penetrate the medium either up to a pre-defined maximum depth or until a maximum level of resistance (which can be soil specific) was reached. Thus, a pressure-dependent outline of objects within a medium can be obtained. Since the resistance encountered by each probe can be monitored and recorded, a three-dimensional resistance map of the medium can be obtained. Also, an array of probes can be tilted with respect to a previous sampling direction and the medium (and objects within the medium) can be examined from additional views. Just as it is possible to implement versions of tomosynthesis (or CT) using acoustics, optics, and ionizing radiation, a version of tomosynthesis (or CT) based on resistance measurements can be employed.

The insertion of the probe(s) into the obscuring medium offers new options. An acoustic probe (a probe which incorporates one or more transducers or photo-acoustic sources) can be inserted into a hole created by a conventional probe, and the concealed object (at a particular location), if present, can be ensonified. If the acoustic probe is sufficiently sturdy, then it can also be used to form a hole without the aid of a conventional probe. In a similar manner, other probe designs (optical, ionizing radiation, magnetic, electrical, passive acoustic detector using a fiber optic interferometer, chemical sensors, etc.) and devices (drill bits, screws, magnetized markers, transmitters, penetrating projectiles, fiber optics, electrical wires, heat and cold sources, tubes to transport gases, liquids, chemicals, radioisotopes, and agents) can be inserted into the hole. A probe and surrounding probes can be used as radiation sources and/or receivers. For example, an acoustic probe can be created by incorporating transducers or readout mechanisms into a probe. Probes can also be used as sources and/or receivers in conjunction with external sources and receivers. Transmission and backscatter measurements can be obtained internally and externally. Another implementation of this concept is to have a probe tap (at a selectable rate) the surface of the unknown object and then allow the probe and/or other probes near or in contact with the object to listen to the transmission of sound. Non-acoustic options include using probes made from conductive materials, ferromagnetic materials, or magnetic materials, etc. For example, parameters such as conductivity might be measured. Thus, probes can have specialized functions if desired.

Contact and non-contact sources and receivers can be employed for imaging concealed objects in an obscuring medium. For example, a non-contact data acquisition format for detection of buried mines which uses optical (electromagnetic) radiation differs from existing systems (such as ground-penetrating radar) by emphasizing the use of collimation (including time-resolved techniques) for source and/or receiver, a range of source waveforms and beam properties (spectral content, coherence, polarization, etc.), the use of multiple beams, angled beams (and virtual beams), appropriate reconstruction techniques, and/or the use of coupling materials as well as surface modifications. The source and receiver can also be used in contact mode. It is also possible to use diffusive wave techniques in which case the source and receiver can also be used in a contact mode. Contact optical and acoustic diffusive wave imaging techniques for human tissue, a scattering, absorbing, and distorting medium, using a coupling material have been reported. See, Nelson et. al., U.S. patent application Ser. No. 08/480,760, filed Jun. 6, 1995, and U.S. patent application Ser. No. 08/597/447, filed Feb. 2, 1996.

A conventional non-contact acoustic data acquisition system would employ an acoustic source in air and would use a laser Doppler readout technique by scanning the surface. This is extremely inefficient with regard to coupling acoustic energy into the ground and provides a readout with poor spatial resolution and a highly variable signal to noise ratio. See, e.g., A. Berni, Remote Sensing of Seismics Vibrations by Laser Doppler Interferometry, Geophys., vol. 59, no. 12, pp. 1856–1867 (1994) (using stationary contact sources). This design can be improved by the use of coupling materials and a reduction in surface roughness and irregularities. It can also be improved by generating the acoustic source at or below the surface using the photo-acoustic effect (the optical waveform penetration depth will depend on the structure of the surface and medium materials for a particular optical beam spectrum and power). Energy coupling into the medium is efficient and the source can illuminate a relatively small volume compared to an air-coupled source. The photo-acoustic effect will also generate a thermal signal. The propagation of this thermal signal can also be recorded and analyzed. A coupling material can enhance the photo-acoustic effect by reducing surface roughness and irregularities and by altering the local properties of the medium, including the penetration properties of the optical beam. The coupling material can also enhance a laser Doppler readout signal by reducing surface roughness and irregularities and by altering the reflection properties of the surface.

A non-contact acoustic data acquisition format can, in some cases, reduce operator risk while providing an improvement in scanning speed relative to contact methods. There are also instances where a contact acoustic data acquisition format can offer high survivability, efficient energy coupling into and out of the obscuring medium, and low cost. In the case of a data acquisition system design which involves only acoustic imaging, the source and receiver units (i.e., modules) can include, for example, one or more of the following: acoustic transducers, photo-acoustic sources, holographic and laser Doppler receivers. Contact and non-contact sources and receivers can be used together if advantageous. For example, if a photo-acoustic source is inadequate, then an acoustic transducer source can be used with a laser Doppler readout. If a mine explodes, the loss is likely to be limited to one or a small number of transducer sources. A source and receiver can be part of the same module. Modules can be used for one or more of transmission imaging, backscatter imaging, and virtual beam imaging.

An acoustic signal due to a photo-acoustic source can be generated at one or more sites on the surface of a source module and the received acoustic signal can be readout at one or more sites on the surface of a receiver module using, for example, the laser Doppler method. In this case the radiation from the optical source generates acoustic radiation which is then incident on the medium after propagating through a region of the module. The readout surface is preferably highly reflective and well defined. A deformable mirrored deflection plate (similar to that employed in a scanning laser acoustic microscopy i.e., or SLAM) or a reflective elastic layer ot surface can be used to readout the acoustic waveform at the exit surface (which may also be the entrance surface). Such a deflection plate or surface can be integrated into a module. One possible design is to use a deformable mirror coating which is reflective at the readout beam wavelength, but transmissive at wavelengths used for optical (electromagnetic) imaging. The deflection plate or surface itself can function as an acoustic source or detector if it is made from a piezo-electric material such as a piezo-ceramic, a piezo-composite, or a piezo-polymer such as polyvinylidene difluoride or PVDF. See, 1733 SPIE (F. Lizzi, ed., 1992); and G. Kino, Acoustic Waves: Devices, Imaging, and Analog Signal Processing (1987). The acoustic source signal (regardless of how it was generated) can be monitored by the laser Doppler method or by incorporating a transducer into the source module or employing a separate receiver module.

Multi-element acoustic beams can be generated by using an array of acoustic (including photo-acoustic) sources. A system comprised of multiple optical radiation beams can also be implemented. Angled beams can also be used in optical as well as acoustic imaging systems. A large area can be scanned by moving the source and receiver modules or an array of modules can be used to acquire data more quickly. A module can be comprised of acoustic (including photo-acoustic) and optical sources and receivers, permitting the acquisition of acoustic and optical data.

This concept of employing multiple types of radiation can be readily extended to include the use of ionizing radiation. Particular module designs can be implemented based on cost and the specifics of the desired application. Acoustical and optical absorbing coatings or materials can be used to prevent unwanted radiation from reaching the receiver. The module can have a elastic or flexible layer between the source and the surface of the obscuring medium (or a radiation coupling material) or the receiver and the surface of the obscuring medium (or coupling material). This flexible layer can provide a more-uniform interface by filling voids or discontinuous regions in the medium surface and improving radiation coupling while helping to isolate the source and receiver from direct physical contact (see FIG. 1). The module or imaging module concept is based on the bladder concept presented by the present inventors, Nelson, et. al., U.S. patent application Ser. No. 08/597/447, filed Feb. 2, 1996. Imaging systems which use ionizing radiation (gamma rays, x-rays, neutrons, and to a lesser extent charged particles) can benefit from the techniques described previously.

In the background discussion the use of reference objects such as guide stars is mentioned. It will be shown that the concept of a reference object can be used to enhance imaging of concealed objects in obscuring mediums through invasive and non-invasive methods. This will require (for a medium such as soil) inserting an appropriate reference object (such as a sphere, a plate, a model of the concealed object, etc.) into the medium and imaging it actively or passively. An alternative is to create a reference object such as a bubble or other anomaly in the obscuring medium and image it.

DETAILED DESCRIPTION OF THE PREFERRED EMBODIMENTS

Figure 1:
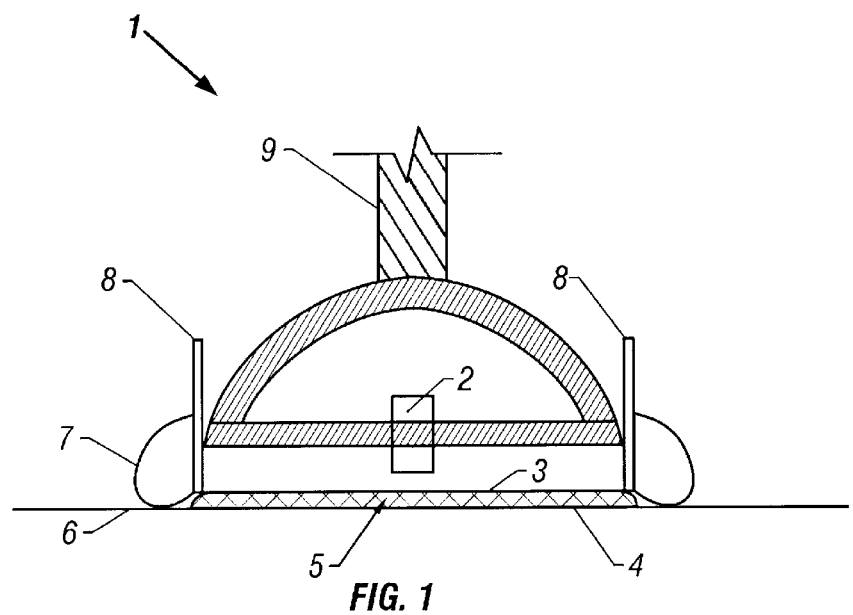
FIG. 1 is a cross sectional view of an acoustic imaging module 1 comprising one or more transducers 2 within a bladder or bag 3 containing an acoustically-transmissive coupling material 4. The contact surface 5 of the bag 3 is preferably flexible and acoustically-transmissive. Preferably, a layer of coupling material 4 connects the bag 3 with the surface of the medium to be scanned 6. An optional flexible sealing ring 7 helps to maintain the continuity of the layer of coupling material 4 while image data is acquired. The sealing ring 7 can be a closed unit or an adjustable unit that can be pressurized (using a liquid or gas). Two optional injection tubes 8 are shown to feed additional coupling material 4 into the layer between the surface 5 of the bag 3 and the medium surface 6. A support frame 9 can be used to move the imaging module 1 and ensure adequate contact pressure with the surface of the medium 6.

The present invention is directed to enhanced imaging systems for locating and identifying objects concealed by an obscuring medium. The embodiments of the present invention shown in FIGS. 1–5 and 7–9 utilize one or more of an acoustic (including a photo-acoustic), optical (electromagnetic), and ionizing radiation source to produce a beam or a number of beams which, in turn, are used to obtain images of the obscured object.

Since many versions of this invention are possible, for those implementations which use radiation sources such as acoustic (including photo-acoustic), ionizing, and optical radiation sources, the requirements can range from continuous (for example CW or modulated CW (AM, FM)) to rapidly pulsed and thus may include coded, and complex waveforms. Controlling parameters such as the radiation pulse width, the degree of collimation (including the angular distribution, and the dimensions of the input beam), the frequency and spectral composition, the phase, the amplitude, the coherence, and the degree of polarization of the radiation are methods of encoding or restricting the properties of the radiation source. A number of collimation methods (e.g. by gaps, coupling materials, mirrors, refractive and diffractive lenses, fiber optics, light pipes, masks, coded or patterned apertures, mechanical apertures, grids, polarized filters, narrow spectral bandwidth filters, directionally-sensitive filters, spectrally-sensitive and directionally-sensitive filters (including multilayer optics, crystals, powders, interferometers, etc.), electronic focusing, waveguides, capillary optics, focused arrays, holographic or diffractive spatial filters as well as acousto-optical devices which exhibit high angular sensitivity, reciprocating collimators, reciprocating grids, etc.) are available for enhancing image quality.

The beam dimensions can be reduced by limiting the cross sectional area of the beam (a conventional method of collimation) and by limiting the temporal width of the beam (i.e. using a short pulse width or a short coherence length) and, thus, limiting its spatial extent along the direction of propagation. The effect of reducing the cross section of the radiation beam is equivalent to adding a spatial filter since it can help to limit scatter cross-talk within the beam itself.

The waveform emitted from the radiation source can also be controlled. A number of phase, frequency, and noise-resistant coded waveforms (for example, chirp pulses) have been used in radar and acoustics (ultrasound, underwater, geophysical) (see, e.g., D. Wehner, High Resolution Radar, Chapters 3 and 4, (1987); G. Kino, Acoustic Waves: Devices, Imaging, and Analog Signal Processing (1987)), in optical communications (e.g., a "complex" waveform such as a soliton pulse), in electronic communications (see, e.g., H. Rowe, Signals and Noise in Communication Systems, (1965); and C. Nagasawa, et al., Applied optics, vol. 29, no. 10, p. 1466–1470 (1990)), and in encryption, and can be applied to imaging of concealed objects in an obscuring medium. Such waveforms permit decoding (for example, matched filter and matched field processing are often used in underwater acoustic signal processing) of the active or passive transmitted signal (where appropriate) and/or the active backscattered signal and, thus, allow a comparison of how beam properties such as coherence, amplitude, spatial distribution, phase, spectrum, polarization, and relationships between pulses (for example, pulse patterns or sequences) or wavefronts, etc., are modified by the environment through which the beam passes. Adaptive beam forming techniques and filters (see G. Kino, Acoustic Waves: Devices, Imaging, and Analog Signal Processing (1987)) can also be used.

A radiation source can be frequency or amplitude modulated using a specific waveform or pattern. Thus, sinusoidal wave amplitude modulation can be employed to measure information about wavefront propagation for conventional imaging methods and diffusive wave imaging (see FIG. 5). The effect of the obscuring medium on a complex waveform (such as a source of soliton pulses and an appropriate collimated receiver which can include a fiber amplifier) can also be evaluated. Temporal or phase properties of a pulse or wavefront can be utilized to provide additional beam collimation. A number of time-resolved optical imaging techniques have been developed for use with highly scattering media, ultrafast phenomena, etc. These applications exploit temporal or phase properties of the radiation field (e.g. time-of-flight, holography, heterodyne, homodyne, Raman amplification, etc.). If the electromagnetic radiation source is pulsed and the pulse length is sufficiently short, techniques such as gating can be employed in conventional TOF imaging and analysis (typically based on the "ballistic" and sometimes the "snake" component of the radiation field). The ballistic, snake, and diffuse components of the signal (the temporal profile) can each be acquired and evaluated independently if desired. TOF imaging using acoustics has been available for a number of years. Speckle and holographic interferometry imaging can also be employed (P. Hariharan, Basics of Interferometry, Academic Press, Inc. 1992; J. Briers, Laser Doppler and time-varying speckle: a reconciliation, J. Opt. Soc. Am. A, Vol. 13, No. 2, pp. 345–350, 1996). Scatter correction measurements can be used to reduce noise in the detected signal in addition to any collimation in use.

Advanced statistical techniques can be applied to available information concerning how various obscuring media affect the temporal profile, phase, amplitude, spatial, polarization, and spectral content of the radiation waveform or pattern. In some situations a reference image or profile can be acquired in order to correct for the effects of a rough and irregular surface and other environmental sources of noise (for example, a laser Doppler readout is acquired before and after an acoustic pulse is launched) or the effects of the medium itself (for example, prior to the introduction of a coupling material into the obscuring medium) on the radiation waveform. Distinct reference images for each region of the medium surface or the medium itself which is to be imaged may not always be practical. An alternative is to acquired appropriate single or composite representative reference images for the medium surface or the medium which can be applied to all the image data. A reference image of the readout surface can also be used with interferometric techniques. The concept of a reference image can be extended to include the use of a reference object with known properties which would be introduced into the medium. Reference images could then be acquired using the various imaging methods described herein. These reference images would more accurately depict the complex problem of imaging a system comprised of a concealed object in an obscuring medium. Reference objects can also be used for passive imaging applications were radiation emitted from a concealed object is detected. In this case the buried reference object can be induced to emit radiation in the same manner as an actual concealed object would be induced to radiate or a source of radiation similar to the emitted radiation can be incorporated into the reference object prior to burying it. A simple version of a reference object which might simulate a point-like source (or some other source distribution such as a plane wave source) assumes the role of a guide star. The information acquired by imaging the guide star reference object could then be used to help compensate for medium-dependent effects which modify radiation propagation.

Figure 2:
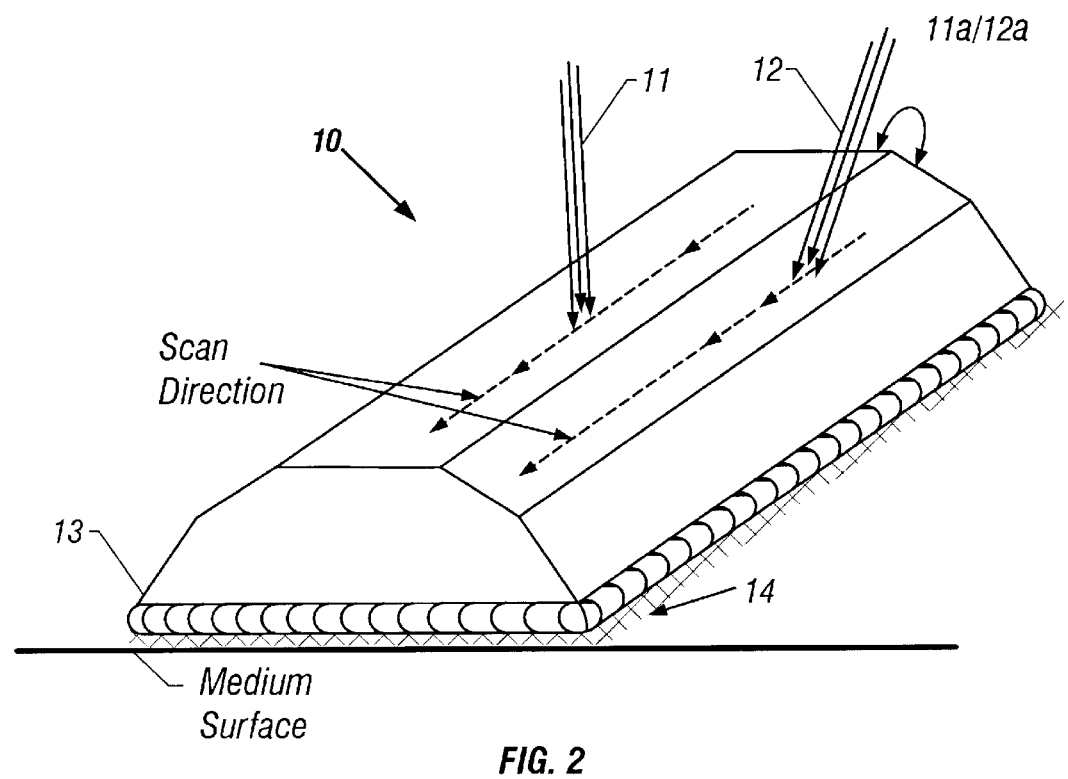
FIG. 2 shows a remote imaging module 10 similar to that shown in FIG. 1, but without a support frame, sealing ring, or injection tubes. This implementation uses a photo-acoustic source beam 11 and an optical readout (laser vibrometry) beam 12. The module 10 can scan from several angles (permitting angled beams) and it comprises an acoustically-transmissive material. Preferably, the readout surfaces 11a/12a are reflective for the readout beam 12. This embodiment also may include a flexible layer 13 and a coupling material 14. Another implementation of this design using optical radiation includes a module 10 which is optically transmissive at desirable wavelengths. In this case the readout consists of scattered optical radiation.
Figure 3A:
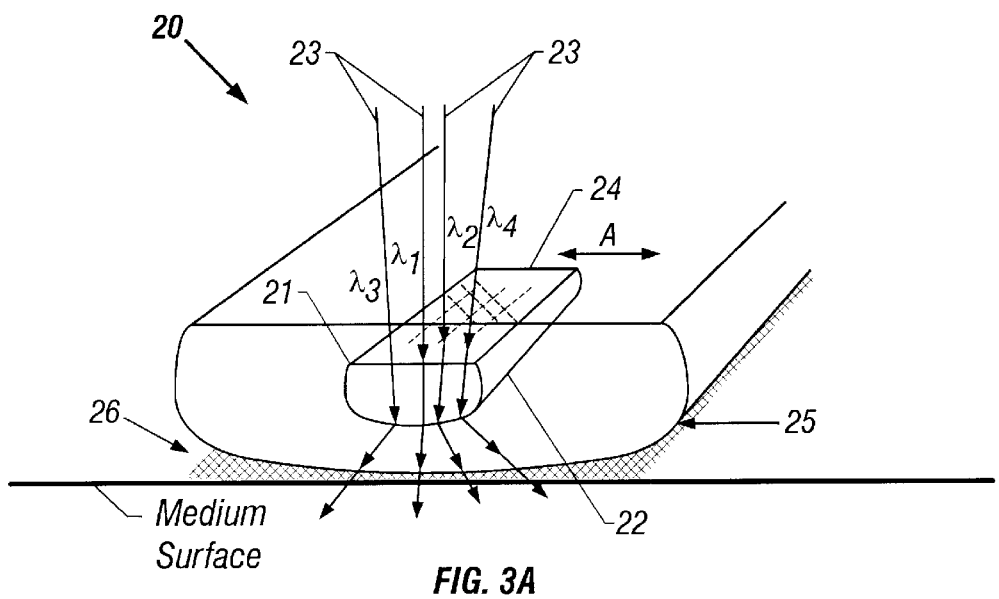
FIG. 3a shows a perspective view of an imaging module 20 which can be used to acquire optical angled beam data for multiple source wavelengths. A lens unit (or other suitable optical device) 21 can scan (i.e., move) laterally (see arrow A) and the face 22 of the lens 21 can raster scan using one or more optical beams 23 thereby creating a beam raster scanning pattern 24. This embodiment also may include a flexible layer 25 and a coupling material 26.
Figure 3B:
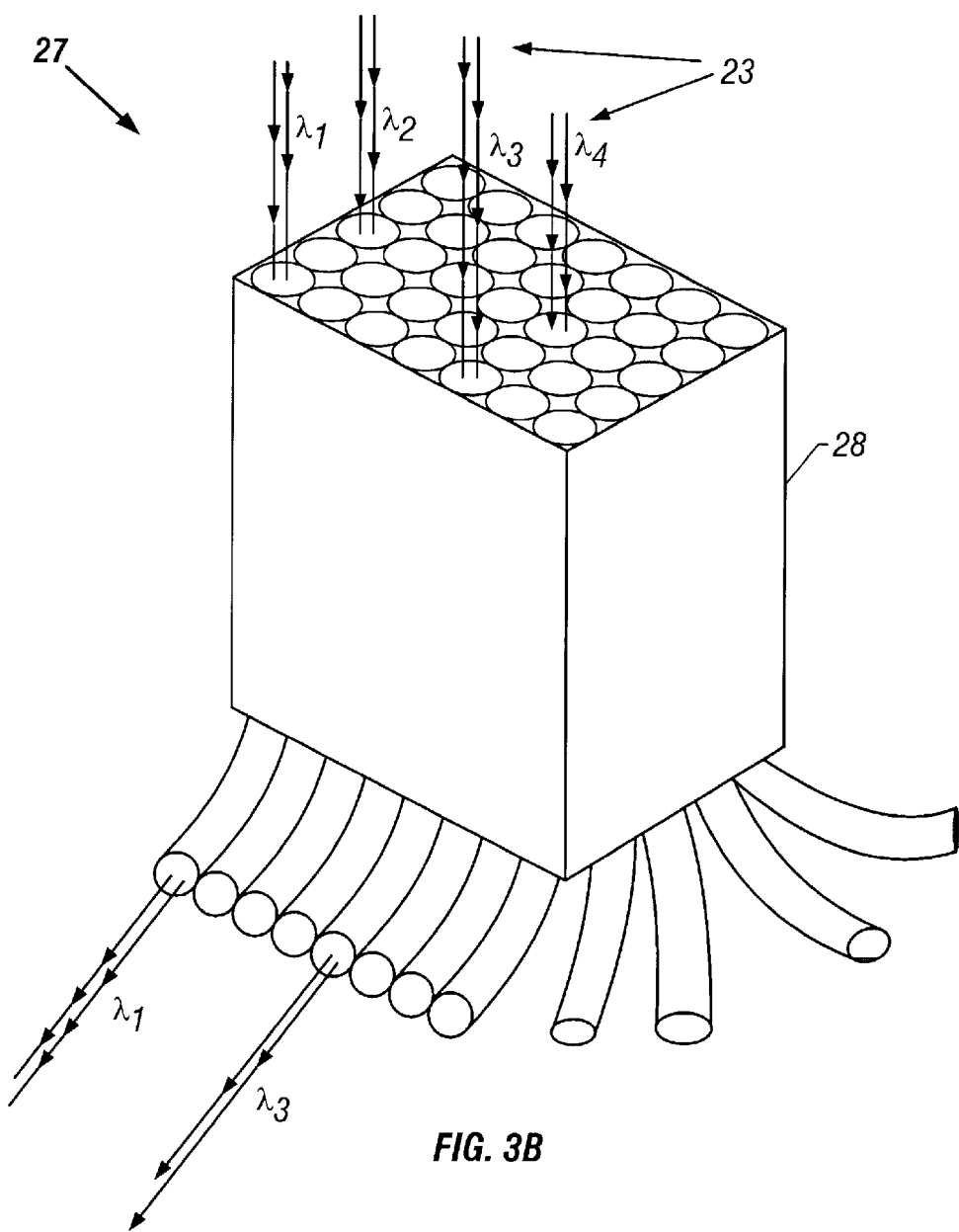
FIG. 3b shows a fiber array 27 comprised of a bundle of angled fibers 28 which can be used in place of the lens 21 in the embodiment shown in FIG. 3a to acquire optical angled beam data.

The present invention also relates to imaging concealed objects within an obscuring medium using multiple collimated angled radiation beams, including normal incidence (see FIG. 2, FIG. 3). A number of designs can be used to direct (or restrict) source, transmitted, and scattered radiation including lenses (optical, acoustical), mechanical, coded, or patterned apertures, grids, masks, fibers, mirrors, beam splitters, the source geometry, the detector geometry, absorptive materials, etc. (see, Nelson, et. al., U.S. Pat. No. 4,649,275 (Mar. 10, 1987), U.S. Pat. No. 4,767,928 (Aug. 30, 1988), U.S. Pat. No. 4,829,184 (May 9, 1989), U.S. Pat. No. 4,948,974 (Aug. 14, 1990), U.S. application Ser. No. 08/480,760, filed Jun. 6, 1995, and U.S. application Ser. No. 08/597,447, filed Feb. 2, 1996).

Images can be reconstructed by conventional methods such as beam forming, holography, etc., or more advanced methods (such as tomosynthesis or CT) can be implemented. These beams can have different characteristics and need not sample the same region at the same time. Thus, a single beam can scan a particular location from a plurality of angles in succession. Multiple beams (which can be point, line, or area type) can scan a particular location over a range of angles at the same time or at different times. In addition, angled scanning can be implemented using more than one scan direction and even complicated scan patterns can be implemented. Similar scanning techniques are employed in x-ray tomography (see E. Christensen, et al., An Introduction to the Physics of Diagnostic Radiology, (1978)). Separate angled images can be formed from the data or images can be synthesized from all or part of the transmitted and/or backscattered data. Since the data is in electronic form, the process of forming new images from many views can be described as radiation tomosynthesis. Off-axis radiation can be measured and used to correct for scatter contributions to the received signal. Angle scanning need not be limited to a single energy, waveform, or even radiation type.

Tomosynthesis can be viewed as a limited implementation of CT in which the range of acquisition angles and/or the acquisition geometry have been restricted. Nelson, et. al., in U.S. Pat. No. 4,948,974 show how to obtain three-dimensional information by using transmission (if possible) and/or backscatter imaging with a focused beam which has a well-defined depth of focus over a limited range. The focused beam can be thought of as comprising a number of beams which are incident on the medium from a plurality of angles.

An imaging system based on a focused beam implementation of tomosynthesis can acquire multiple image slices by scanning along a plane corresponding to each slice, adjusting the height of the beam waist, and scanning along another plane. Image resolution within a slice can be enhanced by deconvolving the overlapping information from other planes. The scanning geometry of a focused beam need not be restricted to a plane parallel to the surface or even a plane. Complex scan geometries can be implemented, of which many are known in the field of tomographic radiography. Scanning through multiple depths with a focused optical system is relatively straightforward. In the case of a focused acoustic system which uses a lens or a series of fixed intersecting beams, a column of coupling material of adequate height (to span the range of depths which need to be interrogated) should be present. This requirement can be modified if the array elements can be repositioned and/or the beams can be tilted so as to move the focus position.

Discrete angle scanning can provide better control for image reconstruction (multiple discrete images will already exist) as well as improved scatter correction capability. As was mentioned previously, complex scan geometries can also be synthesized from discrete angled beams. The discrete angle scanning approach permits more effective use of virtual collimated transmitted or backscattered radiation in comparison to when a focused beam is employed. Tomosynthesis based on a focused beam or discrete multiple scanning angles can be implemented with the various waveforms described previously (CW, pulsed, coded, complex, CW-modulated, time-resolved, etc.). In addition, diffusive wave tomosynthesis can be implemented. If data from a sufficient number of view angles can be acquired, CT reconstruction techniques can be utilized.

Virtual transmitted and backscattered collimated radiation beams can be generated from angled beams and can be used for imaging and/or image enhancement (virtual tomosynthesis, virtual CT). These virtual collimated beams can be useful since they appear to originate from below the surface of the medium being imaged. A source which appears to originate from within the medium can illuminate a region from a different perspective than an external beam. Thus, three-dimensional image information can be synthesized using data acquired from multiple projections. This information can include data from the multiple collimated angled beams (transmitted and backscattered) and/or the multiple virtual collimated beams. Since the source requirements can range from CW to rapidly pulsed, various time-resolved, CW, and modulated-CW (such as diffusive wave) radiation imaging techniques, or radiation techniques which use a coded or complex waveform can be used with the angled collimated beams and the virtual collimated beams imaging techniques.

The ability of an imaging system to localize the presence of an object due to its physical properties (including characteristic signal patterns or signatures which may be due to a resonance condition, reradiation, a radiation pattern which is the result of its physical structure, its physical structure in conjunction with the surrounding environment, its material composition, Doppler effects, etc. as well as reflection, scattering, and absorption) can be enhanced by the use of multiple angled beams. See Image Recovery Theory and Application (H. Stark ed. 1987).

The present invention also relates to acquiring additional information about object or medium characteristics by intersecting an acoustic radiation field with an optical radiation field (i.e., creating an acousto-optic effect). An acoustic source (such as a transducer, photo-acoustic device, etc.) can be used to create an acoustic radiation field within a particular volume of the medium (for example, homogenous or inhomogeneous mediums such as soil, organic material including tissue, a body of liquid or gel, man-made objects such as pipes, walls of buildings, packages and luggage, etc.). The acoustic field alters the optical properties of the various materials within that volume.

A variety of acoustic waveforms and sources can be utilized, as is well known in geophysics, ocean acoustics, photo-acoustics, and ultrasound. The high resolution optical scanning techniques described previously can be implemented. The acoustic field can be employed with focus beam optical imaging methods as well as multiple discrete-angle beam optical tomosynthesis (or CT) techniques. Changes in the amplitude and characteristics of the transmission and backscatter radiation, which may include the presence of Doppler-shifted radiation, can be evaluated with the acoustic field present and with the acoustic field absent. If the spatial extent of the acoustic radiation field is reasonably well-defined, the intersection of the optical beam at an appropriate angle to the acoustic field provides three-dimensional information since the interaction volume is approximately described by the intersection of the two fields. Thus, acousto-optical transmission and backscattered tomography is possible.

As described earlier, source requirements can range from CW to rapidly pulsed. The use of acoustic radiation fields with optical radiation fields can aid in the identification of static and dynamic structures as well as the identification of the material composition of the structures. The dynamics of the acoustic field can be followed by observing when optical field parameters, which may include the presence of Doppler-shifted radiation, at one or more locations change relative to the start of the acoustic field (as in a TOF technique) or relative to modulation of the acoustic field. The dynamics of the acoustic field can be monitored with one or more collimated angled or virtual beams or by observing changes in speckle patterns, scatter patterns, etc.

The acoustic beam can enter the medium at normal incidence or be tilted with respect to the surface. The acoustic beam can be focused (collimated) with an acoustic lens and apertures, by using a shaped or curved transducer, or by techniques such as TOF, synthetic aperture imaging, holography, or electronic beam forming using phased arrays (also referred to as electronic collimation) which is widely used in medical ultrasound. See, Christensen, et al., An Introduction to the Physics of Diagnostic Radiology (1978). It is also possible to scan the medium with a number of focused acoustic beams either by using a combination of multiple sources with multiple lens units or a collimated acoustic source with a mask or a coded or patterned aperture (in a manner similar to the corresponding optical technique described in Nelson, et. al., U.S. Pat. No. 4,649,275 (Mar. 10, 1987)). This acoustic raster technique can also be implemented without an intersecting optical radiation field. A collimated acoustic receiver (which can also act as a source) can be used to detect the exiting acoustic radiation field.

Just as optical tomosynthesis (or CT) is possible using multiple collimated (focused) angled optical (radiation) beams, so acoustical tomosynthesis (or acoustical CT) is possible from multiple collimated (focused) angled acoustic beams. The collimated acoustic beams can be electronically or mechanically scanned through a range of angles and the acoustic source (and receiver) can be scanned or translated in the same manner as the optical source (and receiver). Several acoustic sources can be used together to set up complex propagating wave fronts, standing wavefront patterns, or compensated wavefronts (such as time reversal mirrors, a self-adaptive technique) which can improve imaging. See SPIE vol. 1733 (F. Lizzi, ed., 1992); and M. Fink, Object Detection and Imaging with Acoustic Time Reversal Mirrors, SPIE vol. 1942, p.256–267 (1993).

The idea of an artificial laser-induced "guide star" (a simple type of reference object) is already in use in the field of astronomy as a passive technique for correcting wavefront distortions due to propagation through the refractive turbulence of the atmosphere. Passive and active implementations of the reference object concept can be employed for acoustic imaging and optical imaging. An appropriate reference object can be introduced into the medium and acoustically ensonified. Appropriate reference objects might be air bubbles or a cavity, a sphere, a plate or even a reference object with a composition and structure (or shape) like the type of concealed object being sought (such as a mine, a pipe, ordnance, etc.). The received acoustic data can be used to enhance the beam wavefront adaptively or electronically and can aid in determining general properties of the medium. If the concealed object is known to radiate or can be stimulated to radiate acoustically, then a reference object with similar properties (or even an acoustic source) can be introduced into the medium.

The acoustic reference object or guide star concept can be applied to the case where optical or ionizing radiation imaging is utilized (an optical or ionizing radiation reference object or guide star). The number of reference object or guide star measurements required for a particular area is dependent on the degree of homogeneity of the obscuring medium. For example, only a few guide star measurements might be needed in a region covered by a homogeneous layer of sand. One additional benefit of using a reference object which is similar to the concealed object (or class of concealed objects) is that this known signature or reference image can then be correlated with signatures or images acquired during an actual search. Reference object measurements can be made for more than one orientation of the reference object and from multiple beam angles.

If the surface of the medium or a module coupled to the medium is read out optically (or where a coupling material will be added to the medium), then it can be useful to acquire a reference image(s) (typically prior to image acquisition) in order to compensate for or estimate the signal contribution from the surface and/or interior of the medium (as well as environmental effects). A reference image of the readout surface can also be used with interferometric techniques. In some cases the reference image(s) may simply be a composite which is assumed to be representative of a larger region which is to be scanned. Acoustic reference images can also be acquired. A reference image(s) can be compared with newly acquired images in order to look for differences which might indicate the presence of an object.

In addition, virtual collimated (focused) acoustic radiation beams can be measured along with the transmitted and/or backscattered collimated acoustic beams with the aid of additional collimated acoustic receivers (collimated, e.g., by using devices and methods such as an acoustic lens, physical separation (a gap), apertures or masks, electronic beam forming, TOF, acoustic holography, synthetic aperture imaging, etc.). A variety of acoustic waveforms can be employed and acoustic source requirements can range from CW to pulsed. Coherent acoustic imaging techniques which use TOF principles, beam forming (phased ago array imaging), speckle, and synthetic aperture methods are commonly used in medical ultrasound, industrial acoustics, and underwater acoustics. See Modern Acoustical Imaging (H. Lee & G. Wade, eds. 1986). Synthetic aperture methods are also widely used in radar imaging. See D. Wehner, High Resolution Radar (1987). Types of acoustic sources include photo-acoustic sources (single or multiple scanning laser beams), single transducers, transducer line arrays, transducer two-dimensional arrays, focused transducers, and focused transducer arrays. See Christensen, et al., An Introduction to the Physics of Diagnostic Radiology, (1978); and W. Hedrick, et al., Ultrasound Physics and Instrumentation (1995).

Figure 4:
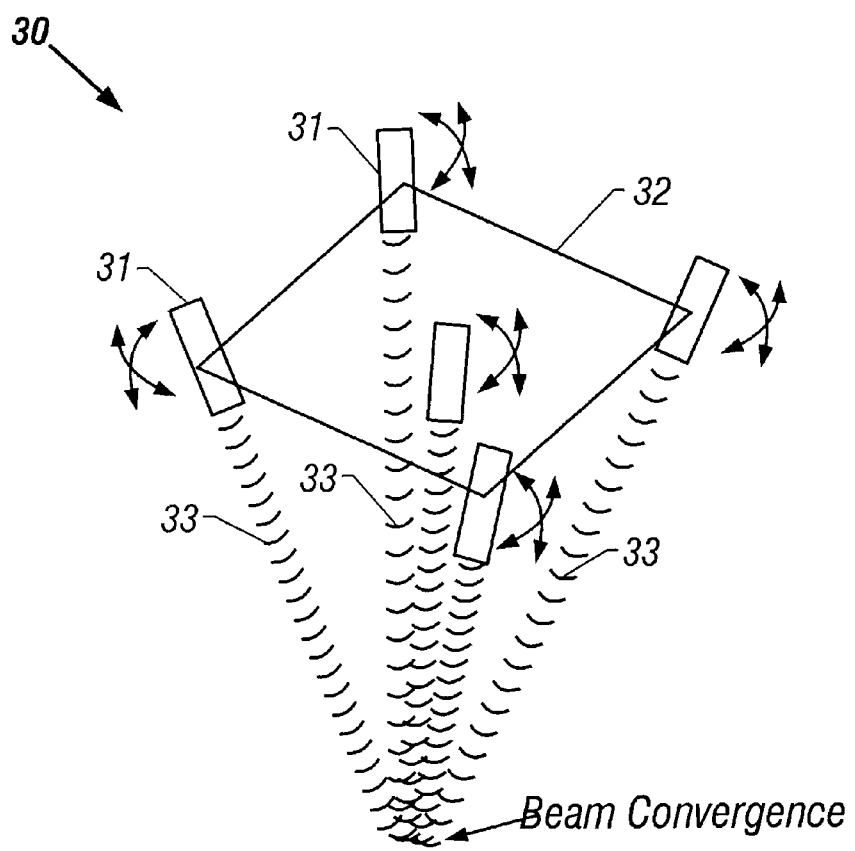
FIG. 4 shows a focused transducer array unit 30 comprising adjustable transducers 31 and an adjustable transducer mounting frame 32. The array unit 30 can be used as part of an acoustic imaging module. Transducer beams 33 are tilted so as to converge at a particular depth within the obscuring medium. Scanning can be accomplished by a variety of means including tilting the transducers 31, elevating/lowering the transducers 31, expanding or contracting the adjustable transducer mounting frame 32, by moving (translating and/or rotating) the transducer array unit 30, or any combination thereof.
Figure 5:
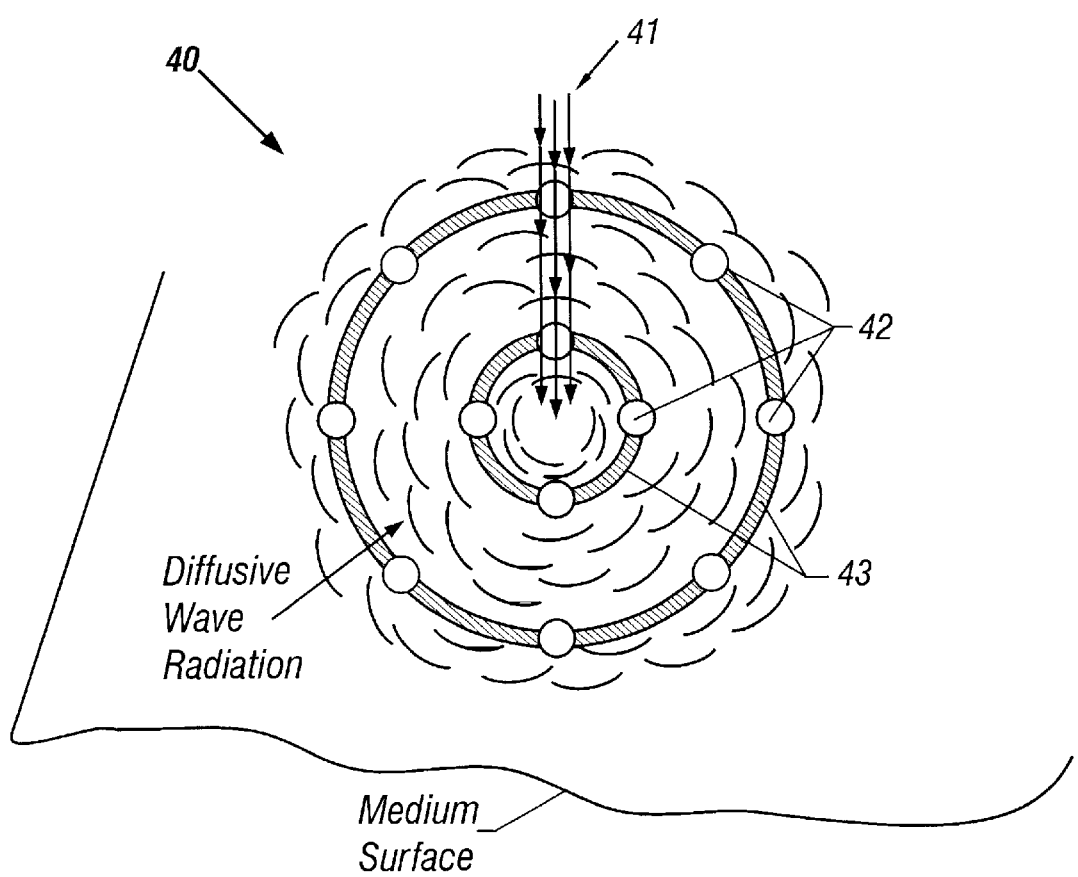
FIG. 5 shows a diffusive wave imaging system 40 including a source of modulated radiation 41 and multiple rings of detectors 42 on frames 43. The system 40 can be used in diffusive wave imaging. The non-contact source (not shown) can be an optical or photo-acoustic source. Detectors 42 can be optical or acoustic detectors. An acoustic module (not shown) can be used in place of a photo-acoustic source.

FIG. 4 shows the use of focused acoustic beams which can be used for imaging, similar to a focused lens optical scanning system (see Nelson, et. al., U.S. Pat. No. 4,948,974 (Aug. 14, 1990)), and to deliver significant power to a limited region within the medium. Optical beams can be used in place of acoustic beams if desired. Medical devices (lithotriptors) with multiple focused acoustic beams are capable of producing sufficient power levels so that kidney stones can be pulverized. Focused optical beams can also be used to produce high power levels at a desired location. The concentration of acoustic or optic power can be used to temporarily or permanently modify the obscuring medium or the concealed object. Imaging can involve observing the effects of these modifications (reradiation, heat, formation of bubbles, changes in scattering, reflection, and absorption, etc.) or their absence. The addition of thermal energy (which can be achieved by a variety of well known methods) may also increase the rate of release of chemicals or gases from the concealed object or the medium and thus can be used to identify the presence of a concealed object.

One acoustic readout method described previously is to use a laser beam of appropriate wavelength to detect the effects of the acoustic field through various vibrometry techniques (as well as using speckle or holographic interferometry imaging) by sampling the obscuring medium surface or a surface coupled to the medium surface. These acoustic data acquisition techniques are now widely used in industry. Two such methods are C-mode and Scanning Laser Acoustic Microscopy, also referred to as C-SLAM and SLAM, and laser vibrometry. See Proceedings, SPIE vol. 2358 Conference on vibration measurements by Laser Techniques: Advances and Applications (E. Tomasini ed. 1994). An imaging module (module), similar to the imaging bladder described in copending U.S. patent application Ser. No. 08/597/447 filed Feb. 2, 1996, can incorporate a readout surface similar to the deformable mirrored deflection plate used with SLAM systems. The module can incorporate a self-sealing material (either as the liquid or gel inside the module or as part of the walls or "skin" of the module) in order to compensate for small holes which can result from contact with the surface of the medium.

Although an acoustic source such as a transducer often serves as a receiver for backscattered/acoustic radiation, additional acoustic receivers can be used to measure transmission, virtual transmission, and backscattered acoustic radiation beams. The detection of radiation with particular attributes (such as a direction vector, localization, etc.) which appears to originate from within the medium is the acoustic analog of imaging with optical virtual collimated beams. The concepts of raster scanning with a focused acoustic source and using off-axis scattered acoustic radiation are well known in the field of industrial ultrasound imaging (e.g., bistatic imaging, multi-path imaging, Synthetic Aperture Focusing Techniques). See J. Krautkramer, et al., Ultrasonic Testing of Materials (1990).

The present invention, as was discussed earlier, also relates to locating and identifying concealed objects in an obscuring medium using conventional diffuse and diffusive wave electromagnetic (optical), acoustic (including photo-acoustic), and acousto-optic imaging techniques. Imaging will typically involve the use of one or more sources and one or more receivers. A receiver or array of receivers can be used to record the diffusive or diffusive wave signal from individual sources. In the presently described technique the level of source and receiver collimation can vary from substantial (using one or more of the collimation means described previously) to limited (collimation is mainly the result of limiting the field of view) and the receivers are used to sample the scatter field over an appropriate area. Sampling densities are influenced by a number of parameters including the type of the radiation, maximum depth, object and medium composition, limits on acquisition time, reconstruction algorithms employed, environmental factors, equipment costs, etc. Similar choices should be made for the tomosynthesis (or CT) imaging techniques described earlier. Thus, diffusive wave as well as collimated information can be used for image reconstruction and data fusion. The concepts of diffusive and diffusive wave imaging can be extended to include ionizing radiation sources and heat (or cold) sources.

The optical or acoustic or ionizing radiation signature (characteristic signal) of an object within an obscuring medium (influenced by factors such as object structure, dimensions, and material composition) may be observed after irradiation from an optical, acoustic (including photo-acoustic), or ionizing radiation source. The object may function as a radiator of acoustical radiation, optical, characteristic or fluorescence radiation, or heat radiation as the result of energy conversion. Conversion to heat energy can result in another type of signature signal which can be used to identify the presence of an object or class of objects. For example, a mine which is buried near the surface and has different thermal properties than the surrounding soil can be identified by temperature contours at the surface when the surface is heated or cooled. See P. Li, et. al., Applied Optics Vol. 34, No. 25, pp. 5809–5816 (1995).

Imaging a concealed object in an obscuring medium via the various methods described herein can be improved by the use of radiation coupling materials (for example, gels or liquids, such as water) in contact with the radiation entrance and/or exit surface(s) of the medium. The radiation coupling material properties (e.g., index of refraction, scattering, and absorption properties) can be selected for a particular imaging format, object or medium type, and/or radiation spectrum. The coupling material can reduce the apparent roughness or irregularity (due to discontinuities, sloping, etc.) of the surface and, thus, improve radiation transport into and out of the medium as well as providing a lubricant, particularly for moving components in contact with the surface. For example, time-resolved techniques (such as TOF) would benefit if a coupling material can be used to minimize the effects of gaps on radiation propagation times. The radiation coupling material, if it can penetrate into the medium (such as soil, sand, gravel, granular or powder materials, materials with a cell structure, etc.), can also enhance the transport of useful radiation (as well as heat or cold) into and out of the region being irradiated.

A coupling material can enhance the use of a photo-acoustic source by providing a more-uniform interface and by altering the penetration properties of the optical beam. The coupling material can also enhance the use of a laser Doppler readout technique by providing a more uniform interface and by altering the reflection properties of the surface.

The coupling material can assume an additional role as a contrast-enhancing material or as a delivery system for agent materials (the coupling material can itself be a aecontrast or agent material) which can improve detectivity. For example, it is possible to observe the transport of water acoustically (or optically or with ionizing radiation) in real time and, thus, detect the presence of an object which distorts the flow or migration of the water. It is also possible to track a pulse or bolus of contrast or agent material as it moves through a medium. The lack of a material such as water in a particular volume may be important for detection purposes. The material may also be used for its radiation absorption properties or its ability to form contrast-enhancing structures such as bubbles (or, for example, to transport bubbles, or transport materials that can produce bubbles).

Various methods of heating a specific volume (such as with microwaves, focused acoustic beams, inductive heating, conductive heating, convective heating) can be used to heat an object or heat the coupling material around the object. For example, localized microwave heating of tissue (diathermy) has been used for hyperthermia in conjunction with ionizing radiation for cancer treatment. The lack of a contrast or agent material (and, thus, a modified heat signature) may be used to indicate the presence of an object. In some cases it may be possible to introduce enough energy into the desired volume such that the object is affected or disabled. An alternative to heating the object and/or the medium is to cool it or them.

The idea of detecting or disabling an object by using the various methods of heating (or cooling) described above to differentiate between the object and the surrounding material (which need not be a coupling material in all cases) or surrounding objects (which comprise the surrounding medium in some instances) can be used for other applications such as scanning packages and luggage (and in some cases even people) for illicit objects. In other instances heating (or cooling) techniques can be used to locate objects such as buried pipes within the ground or within a wall. For example, a gas or liquid within the pipe or the pipe itself can be heated or cooled. In general, temperature changes (heating, cooling) can be introduced using a number of mechanisms including acoustic, optical, and ionizing radiation, electric or magnetic fields (inductive, capacitive, resistive heating), conduction, convection, etc. Typically a data base would be established in order to distinguish the illicit objects from other objects which are likely to be encountered. Thermal images (or even temperature probe measurements) can be acquired before and after the temperature changes are induced. Comparing the image of a perturbed object or medium with that of a reference object is sometimes referred to as differential imaging. Temperature cycling may be employed if advantageous. A series of thermal images can be acquired and compared with a reference image as well as with each other since how the object or medium cool or heat as a function of time may be important and may provide information.

Other imaging techniques can be employed in addition to or in lieu of thermal imaging. If the properties of the object or the medium (or surrounding objects) are altered sufficiently by temperature changes, then acoustic, optical, and ionizing radiation imaging techniques can also be used to detect such changes. Changes in capacitance, resistance, and inductance can also be measured and images can be created from a number of such measurements. Restrictions will apply if human tissue is the medium.

Localized temperature changes may be desirable in applications such as mammography (in which case compression will also be desirable). For example, a focused microwave source can be scanned in a particular pattern to preferentially heat specific limited volumes of tissue. The specific limited volumes of tissue can be interrogated prior to and after heating by an optical or acoustic technique (or various resonance techniques such as MRI). In addition, electron spin resonance (ESR), magnetic resonance imaging (MRI) or the use of superconducting quantum interference devices (SQUIDS) can be used to detect subtle changes due to temperature-dependent effects. ESR, MRI and SQUID-based detection systems may be practical in environments where the orientation of the package, person, etc. is preferably predictable and compensation for extraneous fields is possible (or unnecessary).

A material can function as a contrast material because of its own physical properties or because it transports items such as such as liquids, gases, chemicals, magnetic particles, radioisotopes, etc. which by their presence or absence enhance the ability of the imaging system to detect an object. A contrast material such as water which is introduced into a medium such as soil can be activated by intense acoustic or optical radiation, causing the formation of bubbles which alter the local imaging properties.

A material can function as an agent material or a delivery system for an agent material because the items it delivers to the object or the surrounding medium (such as thermal energy, gases, chemical, radioisotopes, biological organisms, etc.) react with the materials which comprise the medium or the object or which will attach to the object or false objects (for example, decoys or naturally-occurring objects which result in images similar to those of the obscured object being sought) and, thus, raise its acoustic, optical, magnetic, ionizing radiation, etc. profile or otherwise alter surface properties for the interrogating radiation. In some instances the products of the reaction can be detected (including thermal energy). The reaction itself can be a process that can be activated by a radiation source, allowing more control over the particular volume being examined. Activation of an agent by another agent or using radiation such as neutrons is also viable.

In some cases the region with an obscured object can be conditioned prior to the actual search. This may include allowing sufficient time for excess agent material to dissipate or aiding in the removal of excess agent material. If the obscured object or its surface has a porosity substantially different from the surrounding medium, then the object can function as a barrier (alternately, it can function as an absorber or sponge), causing a contrast or agent material to accumulate (or pool) at some region on or near its surface. The obscured object may alter the surrounding medium resulting in compaction or voids where a contrast material might collect. Thus, detectivity might be enhanced through interactions between a contrast material or agent and the object, the medium, or the combined system of object and medium. The use of contrast materials or agent materials (such as a radioisotope, magnetic particles, chemotherapy drugs, iodinated contrast, photo-activated chemicals such as porphyrin, gene therapies, etc.) is well-known in the fields of medical imaging and cancer therapy.

Another method which involves modifying the imaging environment is to redistribute the object and/or the obscuring medium. The objective is to image a defined area of interest, induce the object (or the medium) to shift its position, and then image the area again. A comparison of the "before" and "after" images may indicate a change which would be difficult to detect based on a single image (for example, a change in the background noise pattern or speckle pattern, the obscuring of return signals from other objects, etc.). In the case of a medium such as soil, a vibrating driver or ground pounding device (similar to devices used to pack soil prior to laying a driveway or street) can be used to shake or jiggle the soil. Alternatively, a vibrating device can be inserted into the medium. In some cases this can have the added benefit of causing the buried object (such as a mine or piece of ordnance) to move closer to or penetrate the surface. This may be an effective method to bring objects to the surface such that the problem of detection becomes one of locating surface or near-surface objects. This effect can be enhanced by surrounding (that is, isolating or limiting) the defined area which is to be jiggled or shaken, for example, by inserting a frame or containing wall. The walls of the partially-buried frame (which may be angled) will help constrain the motion of the soil. Vibrating the soil may also result in the detonation of an explosive object (which may be acceptable).

The present invention also relates to the design of an imaging module (module) which would provide a controlled environment for a source and/or a receiver and, thus, reduce the severity of problems associated with transporting radiation into and out of the medium and measuring radiation. The module can be constructed using, in part, radiation absorbing materials. These materials would reduce or limit unwanted radiation from reaching the receiver. A module can be used with acoustic, optic, photo-acoustic, and acousto-optical imaging techniques. A module represents a flexible design for interfacing (either directly or remotely) a source and/or a receiver to the obscuring medium. The module can also incorporate a mechanism for delivering a coating or smoothing material, coupling, contrast, or agent material preferably to (at least) the surface of the medium (although this can also be achieved independently of the module). An optional sealing ring can be used to help localize and retain the coupling material (see FIG. 1). Many aspects of the module concept are based on the implementations of the imaging bladder described by Nelson, et. al., U.S. application Ser. No. 08/597/447, filed Feb. 2, 1996.

A module intended for acoustic imaging can be implemented in several ways. The acoustic source and receiver can be the same device (which is common for medical ultrasound applications where a transducer or transducer array is employed), or the source and receiver can be separate devices. Contact and non-contact sources and receivers can be used together if it is advantageous. For example, certain technologies can be useful for fast, low resolution imaging (sufficient to detect possible candidates) while other technologies can provide slow, high resolution imaging (which can be used to identify whether the candidate is an object of interest). If the density of candidates is sufficiently low, then it can be preferable to scan at two different levels of resolution (or contrast resolution). FIG. 2 shows a relatively simple module intended to be used with an external photo-acoustic source and an external laser Doppler vibrometry, speckle or holographic interferometry receiver. The (non-contact) source and readout laser beams can be delivered to the module by various means including air coupling or a fiber optic wire. The readout surface is a deformable mirrored or reflective deflection plate or surface or elastic layer (such deformable mirrored deflection plates are employed in scanning laser acoustic microscopy or SLAM). The input and readout areas of the module surface can be rapidly scanned, emulating a multiple detector/receiver acoustic imaging system. One alternative is to use a scannerless system with area illumination and a detector array. By slanting input and/or readout devices, angled beam imaging (and virtual beam imaging) can be achieved. Another version of the module incorporates one or more transducers (as a source and/or a receiver) into the module. Angled acoustic scanning beam data acquisition can be implemented (including the use of refraction effects at the boundary of the medium).

A focused beam can be produced by an acoustic lens device (see G. Kino, Acoustic Waves: Devices, Imaging, and Analog Signal Processing (1987)) or by generating a number of source beams at the same time. This can be used for imaging and also for delivering significant acoustic power to the region of interest (see FIG. 4). (As was explained previously, this idea is similar to the approach implemented with a Lithotriptor in which multiple acoustic sources are focused at kidney stones which need to be destroyed. A similar concept involves focusing a number of optical beams at a given depth.) It is possible to monitor the transmitted or backscattered signal as the focused beam is scanned over a region and to monitor the effects that this concentration of power has on the medium, on any coupling, contrast, or agent materials, and on any obscured objects. The effectiveness of the focused acoustic system can be improved for use with a medium such as soil by permeating the medium with a coupling fluid such as water. A simple version of the module has a flexible bottom surface which can be shaped or will conform to the surface of the obscuring medium or a coupling material present on the surface of the medium in order to make good contact.

The module can be designed such that additional coupling material(s) separates the medium surface (or medium surface with a coupling material such as a liquid or gel) from either sources or receivers (incorporated as part of the module) or the input-readout surface of the module. In this case the sheet of material separating the added coupling layer from the medium surface (or the medium surface with a coupling material) can be designed to be relatively rigid or flexible (which would permit the module to conform to irregular and slanted surfaces of a medium). An example of an acoustic coupling material which has been used in sheet form for non-destructive testing is silicon rubber. Thus, a silicon rubber sheet can be in direct contact with a source or receiver or a coupling fluid or gel in direct contact with a source or receiver.

A sheet of material can also function as a transducer if a piezo-electric material such as a piezo-ceramic, a piezo-composite, or a piezo-polymer such as PVDF is employed. Input signal levels (and received signals) can be monitored. Coupling materials may also provide specific scattering and absorption properties as well as providing a physical separation (a gap) between the source and/or receiver and the surface of the medium (which may aid in collimating the acoustic signal in the same manner as an air gap is used in optics or an absorptive dye is used in radiographic x-ray screens to preferentially attenuate light based on total path length traveled).

Imaging modules which use external sources and receivers should be easy to replace and exhibit good survivability characteristics. Modules that incorporate sources or receivers will be more expensive than modules which do not, but they also offer additional imaging flexibility. The incorporated sources or receivers may also be less expensive than the external sources and readout devices. Other factors to consider are environmental conditions, imaging speed requirements, etc. that can be achieved with each version of the acoustic module described. An additional option which can enhance image quality when a module is employed is to utilize a coupling material during data acquisition. A coating or coupling material (such as water) can be delivered to the surface of the medium independently of the module or the coupling material delivery mechanism can be incorporated into the module design. An optional sealing ring around the edge of the module can be used to contain (temporarily) the coupling material (see FIG. 1).

Optical sources and receivers can be used in the same manner as their acoustic counterparts. They can be incorporated into a module or located externally. If they are located externally, then the module functions as a means to provide a uniform detection environment with predictable properties and possibly as a delivery device for a coupling material. The input and readout surfaces of the module can be optically transparent and surfaces can be angled to provide for angled beams (refraction effects at interfaces can also be exploited). Angled surfaces can also be used to produce optical focused beams to deliver energy to a preferred region in a manner similar to the acoustic implementation described. A number of angled surfaces can be present in a module, permitting multiple angled beams (or multiple focused depths) to be imaged as the source or sources are scanned over the module. An alternative is to permit the angled surfaces to rotate and, thus, change the angle of the beam or the depth of focus. An additional coupling layer can be used to reduce the effects of irregular and rough medium surfaces and to provide collimation. Acoustic, optical, and photo-acoustic devices can be used in one system to provide acoustical, optical, and acousto-optical information. See Nelson, et al., U.S. application Ser. No. 08/480,760, filed Jun. 6, 1995, and U.S. application Ser. No. 08/597,447, filed Feb. 2, 1996. Multiple modules can be used to reduce total image acquisition time as an alternative to scanning a single module over the surface of the obscuring medium.

Figure 6:
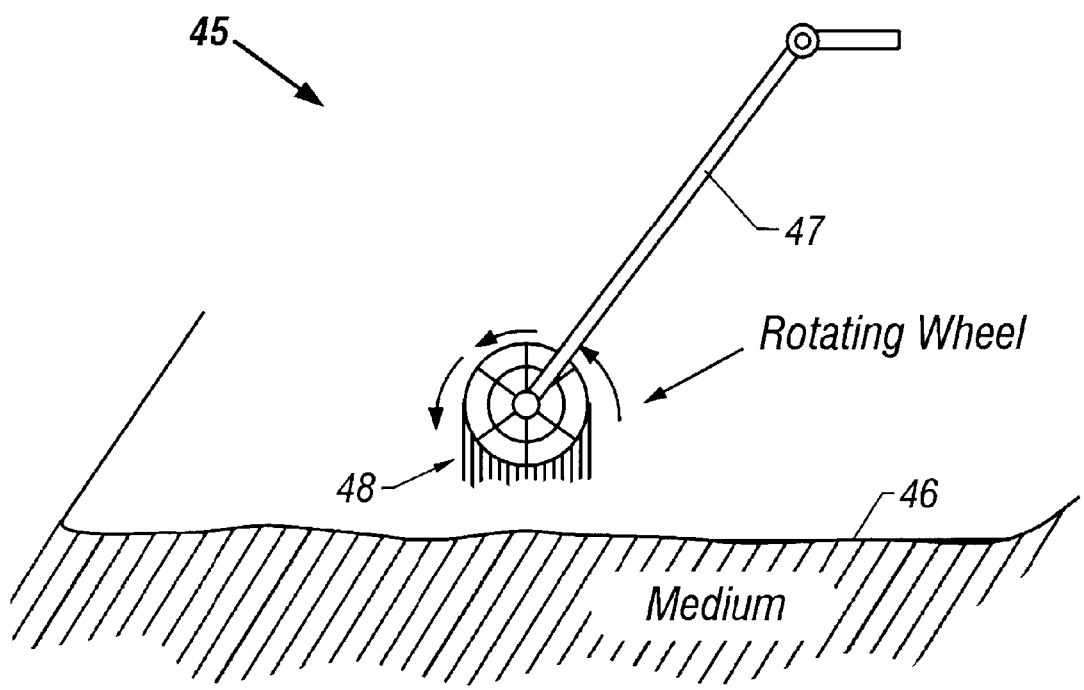
FIG. 6 shows a rotating brush unit 45 which can be used to smooth a surface 46 which is rough or has small irregularities. A support arm 47 can be used to transfer power to a rotating brush head 48. The support arm 47 and brush head 48 can be mounted on a vehicle (not shown) or carried by an individual (a frame with wheels which can be pushed (not shown) can be added to this version if desired). A hand-held version can be used in a manner similar to a powered floor buffer. One variation is to mount a driving motor (not shown) next to the brush head 48 (as is done with a floor buffer) rather than drive it through a belt or cable (not shown). Another variation is to use forced air to cause the brush unit 45 to hover over the surface 46. The support arm 47 is preferably adjustable so that the brush head 48 can dynamically compensate for the contour of the terrain as it moves over the surface 46. An optional air or water jet (not shown) can be used to clear debris, smooth the surface 46, and help uncover objects.

In some situations the surface of the obscuring medium requires preparation before effective imaging can be implemented. Surface preparation can include clearing obstructions, ground cover, and reducing the effects of surface roughness and irregularities. Surface irregularities can be diminished by traditional mechanical means such as rakes. An alternative method to using rakes is to use a surface preparation system based on a rotating brush (similar in concept to a powered floor buffer) to smooth the surface (see FIG. 6). When used in hazardous situations such as mine detection, the brush (which can be attached to an arm that pivots) should offer a small cross section to a blast so that it will suffer little or no damage from an explosion. If it is damaged, it will be simple to replace. Brush bristle design, brush orientation and rotational speed can be chosen so that debris (including surface mines) will be dispersed with a suitable range and velocity (which may minimize damage to the brush from surface mines). One version of the brush has bristles which are capable of shredding debris (including surface mines). A blower or air jet can be used with or without the rotating brush in order to clear debris from the surface (as well as providing a non-contact mechanism for uncovering objects such as mines). A water jet can be used as a substitute for an air jet. A water or air jet can also be used to smooth the surface with or without a brush. Surface roughness and irregularities can be evaluated optically or acoustically in order to determine the need for such corrective action.

Passive or active optical and/or acoustic surface imaging systems can also be used to locate objects such as surface mines or mines that are only partially obscured prior to scanning the medium. Once a concealed object such as a mine is located, a variety of techniques can be used to remove and disable it, preferably with minimal human intervention. Buried mines are likely to be positioned relatively near to the surface (in comparison to the typical dimensions of the mine). One cost-effective solution is to use an arrow-like bolt attached to a cable. The tip of the bolt can be optimized to penetrate or incapacitate the mine, ordnance, etc. The bolt can be launched with an appropriate velocity (using a propellant, spring, etc.) into the soil and skewer the mine. If the mine does not explode while retracting the cable and pulling the mine to the surface, it can then be rendered inoperable (if it is not yet incapacitated).

An alternative implementation is to mechanically drive or drill the bolt into the medium and the object. If drilling is utilized then the bolt shape is preferably that of a drill bit. The simple bolt design can be extended so that the bolt can provide additional functionality (i.e., a complex bolt design). For example, the arrow-like bolt can be easily modified so that it can also function as an electromagnet. This can aid in the retrieval of (or indicate the possible presence of) metal mines or ordnance (which can be located at greater depths). The bolt can also be modified (for example, it can be hollow and provide orifices or windows) to deliver an electric current, heat energy (or remove heat energy), a coolant, liquids (including liquids which have been heated or cooled), gases, chemicals, biological organisms, optical radiation, acoustic radiation, ionizing radiation, etc. which can aid in incapacitating (or even detonating) the mine or ordnance. These modifications to the simple bolt design may require that tubes, wires, and fiber optics be attached to the bolt. The bolt device can be implemented remotely and the components should demonstrate a high degree of survivability or be easily replaced. Thus, a bolt can be made from ceramics, metals, or plastics (or a biodegradable material such as wood, a wood product, or even ice). An extension of the invasive bolt concept (ground-penetrating/contact, destructive), is use of a probe (which permits contact imaging), and will be discussed below.

The imaging system(s) described can be carried (or wheeled) by one or more individuals or mounted on a vehicle (which can be remotely controlled if necessary). A bolt delivery system is preferably mounted on a remote controlled vehicle.

The employment of an invasive tool such as a bolt is primarily useful once an object has been located and successful implementation typically results in the modification (or destruction) of the object. An alternative approach is to use one or more bolts to sample the region, thus avoiding the detection and localization aspects of the problem (this assumes that damaging concealed objects is acceptable). This strategy can be effective in cases where the density of concealed objects is high relative to the total area searched. An enhancement to the bolt concept is the modification of a bolt into a probe which can be used to detect the object. It then becomes possible to penetrate the medium (in a controlled manner) using a probe or an array of probes (for example rod-like or needle-like probes), each connected to its own pressure sensor. Probes typically can execute linear motion and/or rotational motion and can be made in a variety of shapes and sizes. Probes can be rigid or flexible.

One implementation of this device is to use thin, rod-like probes which are needle-like in shape. The spacing of probes within an array would provide appropriate sampling (or sub-sampling) densities. An array can be assembled from smaller arrays (sub-arrays) which need not be identical and can function independently if desired. Probes can have grooves of various designs in their walls to improve penetration through the medium (for example, when probes are drilled into the medium). Various cleaning devices such as narrow apertures, brushes, air jets, etc. can be used to clean the probes when necessary. The rod-like probes are used to penetrate the medium (using a driving or drilling action) either up to a pre-defined maximum depth or until a maximum level of resistance (which can be soil specific) is reached. Probes which can rotate can have clutch mechanisms to protect their motors (similar to the concept used in electric drills). Rotating probes (or drill bits within probes) can also be air-driven, as is done with drills used in dentistry. A pressure-dependent outline of objects within a medium can be obtained. Since the resistance encountered by each probe can be monitored and recorded, a three-dimensional resistance map of the medium can be obtained. A three-dimensional contour map of the surface of the medium can also be acquired.

The probes can be controlled in an adaptive manner. If a probe encounters a maximum level of resistance but neighboring probes do not, then a decision can be made to exceed the resistance limit. Thus, an operator or a computer program can be used to evaluate specific situations. This decision-making capability can also be used to alter a prescribed sampling pattern for an array (or sub-array) of probes. Also, an array (or sub-array) of probes can be rotated about the normal of the plane of the array as well as translated and the array (or individual sub-arrays) can be rotated (tilted) with respect to the normal to the plane. Thus, the medium (and objects within the medium) can be examined from additional views, including multiple angles.

Just as it is possible to implement versions of tomosynthesis (or CT) using acoustics, optics, and ionizing radiation, a version of tomosynthesis (or CT) based on resistance measurements can be employed. Local changes in resistance images can be acquired and used to filter data. Reference resistance images can be acquired and used to filter data. Resistance reference objects based on mine-like objects can also be used if mines are sought. Resistance reference images and resistance reference objects are similar concepts to the techniques already described for use with acoustic and optical imaging formats. Probes can be heated to help penetrate frozen soil. Probes can also act as heat (or cold) sources for analysis of heat propagation or be used to monitor the surrounding temperature.

An alternative to a simple rod-like probe is a flexible probe which can be used to penetrate a medium and then be redirected to move at an angle with respect to the previous direction. Outer shell sections of the probe can be locked together or unlocked as the probe penetrates into the medium, permitting the tip of the probe to move at an angle with respect to the previous direction of motion. The tip would function like a drill bit which is part of a rotating cable that is protected and directed by the outer shell section's geometry. Thus, angled sampling can originate from within the medium whereas the rigid probe approach restricts sampling of the medium according to the line of sight (which can limit the ability of the detection system to see underneath or between objects) Basic medical catheters (which serve a similar purpose) are more limited in that they are (typically) designed to follow a channel such as an artery.

A probe and surrounding probes can be used as acoustic receivers (by connecting transducers or readout mechanisms to the probes) as well as acoustic sources. Probes can also be used as sources and/or receivers in conjunction with external sources and receivers. Transmission and backscatter measurements can be obtained internally and externally. Another implementation of this concept is to have the probe tap (at a selectable rate) the surface of the unknown object, and it and/or other probes near or in contact with the object can be used to listen to the transmission of sound. A variation on this probe design (which will be explained below) would permit acoustic signals to be recorded directly. Other options include using probes made from conductive materials, ferroagnetic materials, or magnetic materials. For example, arameters such as conductivity or inductance might be measured.

The insertion of probes into a medium offers new opportunities. A second probe with a small transducer (or photo-acoustic source if appropriate) near its tip can be inserted into a hole created by a probe, and an object or the medium at a particular depth can be ensonified and recorded. This second probe configuration need not be identical to that of the first probe. This second probe can also include one or more acoustic windows along the (typically) cylindrical walls. A transducer (which can function as a source and/or a receiver) can be coupled to each window. A window describes an area which passes radiation or other items of interest from a source or to a receiver. It can be part of the wall of a probe or it can be an insert into the wall of the probe. A window can have a moveable protective cover.

A possible modification to the second probe configuration is to forgo a transducer at the tip while retaining acoustic windows and corresponding transducers (a third probe configuration). If the probe contains both a transducer near the tip and an acoustic window(s) along its side, then acoustic data can be acquired along the direction of cylindrical axis of the probe and normal (in the radial direction) to that axis. Individual probes can be rotated in place, providing additional acoustic views (similar to the concept of sweeping a spotlight beam to illuminate a region). Previously discussed collimation techniques and waveforms can be employed with sources and receivers incorporated into probes. With the use of an array of such probes three-dimensional transmission and backscatter data can be acquired for image reconstruction using CT or tomosynthesis algorithms. Data acquisition need not be limited to a sequence of parallel planes, as is the case for x-ray CT, since detectors can be distributed in a three-dimensional array (if desired). One or more sources and/or receivers can be incorporated into a single probe and one or more probes can be used for imaging at the same time. This capability may be particularly useful if the probes are inserted into a stratified medium.

In addition, (prior to penetrating the surface of the medium) probes or arrays of probes with transducers can be rotated about the normal of the plane of the two-dimensional array as well as translated. The array (or individual sub-arrays) can be rotated (tilted) with respect to the previous sampling direction. Thus, the medium (and objects within the medium) can be examined from additional acoustic views, TOF, beam forming, diffusive wave, etc. imaging techniques, can be employed. Acoustic resonance conditions can also be investigated. If the second probe is sufficiently rugged, then it can be used to penetrate the medium (eliminating the need for the first probe).

If a probe has an acoustic window, then the maximum penetration depth may be determined by the maximum desired depth for the acoustic window or a transducer located in the tip of the probe. Data can be acquired at a number of depths. A probe can contain a number of windows with single transducer elements or arrays of transducer elements. Although the windows can be flush with the walls of the probe (which in many instances will be approximately parallel with its long axis), the probe can also have angled walls that jut out from the probe body (similar to the way in which the lower stages of a rocket jut out from the upper stages). In this case windows can also be located in these angled walls, providing an additional data acquisition perspective.

In general, probes of various sizes can be used with coupling fluids, can offer good contact with the medium, can be used with an optional flexible sealing ring to help to maintain the continuity of the layer of coupling material while image data is acquired (the same concept which is used with the bladder or bag device shown in FIG. 1, although there is no sealed bag in this case, the transducer(s) is (are) replaced by the probe(s)), a probe can potentially bring the transducer closer to the object to be imaged, and a probe can avoid trying to image through debris, grass, leaves, etc. which may cover the surface. Just as the shape and size of a probe can be optimized for a specific application, other specialized probe designs can be implemented for imaging or recording optical, fluorescence, ionizing radiation; magnetic or electrical fields; establishing the presence of specific materials such as biological specimens, organic and inorganic compounds, gases, etc. (that is, a specialized probe is able to acquire physical samples which can be analyzed within the probe itself or passed on to external diagnostic equipment (using a tube or small container, for example). A number of techniques are in use for analyzing sample materials such as photo-acoustics, mass spectrometry, laser fluorescence, Raman spectroscopy, MRI, fiber or semiconductor biosensors, etc. If an external detector is to be used to receive emissive radiation from an object (fluorescence, acoustic, optical, etc.) then a probe with a similar radiation source can be used like a guide star. This would permit the detection system to make an estimate of the radiation transfer function of the local volume of medium. Such a transfer function could be used to deconvolve the effects of the medium between an emissive object and the receiver. As noted earlier, the guide star concept has been used in astronomy.

The probe would have one or more windows or openings. An optional permeable membrane can cover a window opening if it is desired that a liquid or gas (or perhaps a bacteria) be allowed to enter the interior of the probe. The probe can also have a small cutting tool which can be used to scrape and retrieve for analysis small samples from an object. The probe can also attempt to establish the presence of a particular material using non-invasive sampling methods such as activation using optical or ionizing radiation, radiation transmission, backscatter, diffusion, and absorption properties of surrounding medium or medium between probes, etc. Thus, probes can be used to image the presence of particular materials just as they can be used to image the presence of objects such as mines. Probes can also be used to deliver or measure heat energy (or cold), etc. As was explained earlier, if a probe leaves a hole, a sampling tool like a tube (essentially another specialized probe) can be inserted into the hole which can then be used to collect a liquid, gas, or soil sample (rather than incorporate such a tool into a probe). The presence of a coupling material or agent might improve detection efficiency since materials of interest may be soluble in the agent.

The ability of a probe to search below a medium surface for the presence of particular materials is significant since the techniques currently in use tend to give ambiguous results or are easily defeated with very low cost countermeasures. Consider trying to detect the outgassing of explosives or the casing materials of the explosives (such as a buried mine). The gases might be detected using dogs (olfactory detectors), various types of gas spectrometers, etc. which would sample gases above the surface. Problems exist because the gas need not vent directly above the object, the gas tends to dilute as it moves away from the object, and the presence of dust, etc. which need to be filtered prior to analyzing the sample (and the effects of the wind if the surface is not isolated from the wind). An additional problem is the presence of man-made materials that could overwhelm the sensor. Thus, a field may be littered with plastic, spent shells, residue from various explosions, etc. which are all outgassing and might result in positive detections at every sampling location. The problem can be much worse if someone intentionally contaminates the surface by distributing fine plastic or explosives granules over an area. The contaminant would be very inexpensive, could last for years, is trivial to disperse, and may even obviate the need to actually plant mines in a given area. To defeat the "material sampling" aspect of the probe detection system requires a much greater effort since one must contaminate the medium below the surface. Even if the chemical sensing capability of the probe system is rendered ineffective, the probe system has other capabilities for detecting and locating an object such as a mine.

Many variations of the probe design are possible. For example, an array of small magnetometer probes can be used to record magnetic field variations. Probes can incorporate or be comprised of various tools and devices such as optical, acoustic, and ionizing radiation sources and receivers, electromagnets, beacons or transmitters, fiber optics, electrical wires, inductive devices, cooling or heating sources, tubes for delivering or injecting chemicals, gases and liquids (which can be pressurized), radioisotopes, agents, cooling or heating liquids, or tubes for removing materials or samples. This is in addition to the mechanical probes already described (rigid, grooved, flexible, etc.).

In some cases these devices can be used to alter the medium surrounding the object which can enhance the imaging process or aid in removing (or neutralizing) the object. Properties such as electrical resistance or inductance can be measured by a probe or between probes. The functions of these devices can be incorporated into a probe if desired. A probe or probes can have the capability of penetrating the surface of a concealed object such as a mine and, thus, exposing it to further attack or rendering it harmless. Probes can be used to deliver a current or electrical charge (or ionizing radiation, an intense optical pulse, etc.) to alter a concealed object (and in some instances disable or detonate the object). Probes can be used to heat or cool a concealed object and, thus, make it detectable using a thermal imager or (with sufficient heating or cooling) disable the suspect object.

Another example of a specialized probe design is a probe that can incorporate one or more sources and/or receivers of ionizing radiation (such as x-rays, gamma rays, and neutrons). For example, an isotope source can be located inside a hollow probe. An alternative is to place a target inside the hollow probe and strike the target with electrons, generating x-rays as is done with various x-ray tube designs. Still another technique is to use a capillary optic to pipe ionizing radiation to a window (or tip) or to collect ionizing radiation and deliver it to a detector. The hollow probe can also contain ionizing radiation detectors or, alternatively, a probe might only contain ionizing radiation detectors, functioning only as a receiver. The concept of ionizing radiation windows is similar to the idea of acoustic radiation windows. Thus, the opportunities described for probes which include transducers (and photo-acoustic sources), as well as additional capabilities which result from interaction of ionizing radiation with matter (such as fluorescence or activation analysis) can be utilized in probes which exploit ionizing radiation.

Yet another variation of this concept is the use of specialized probes which act as sources and/or receivers of optical radiation. Fibers, mirrors, waveguides, etc. can be used to deliver and collect low-energy radiation. Alternatively, one or more small sources and receivers can be incorporated into the probes. Probes can also be used to record thermal conditions of the medium or object at one or more positions. In general, many types of specialized probes can be implemented to measure various physical properties of the object and medium. Probes can also be used as receivers for external radiation sources which have already been described. Similarly, probes can also serve as sources for external radiation receivers (and/or serve as guide stars if desired). Thus, a medium can be sampled from additional views when probes are utilized with external radiation sources and/or receivers. Probes can be used to look for chemical indicators which suggest the presence of a concealed object in addition to their use in imaging systems. In some cases a sample of the medium must be modified before a particular chemical signature can be measured. For example, a probe with a window can be used to deliver an intense beam of optical radiation which heats or vaporizes a small volume of soil. Chemical compounds of interest can then be analyzed using various techniques such as those mentioned earlier (e.g., fluorescence, spectrometry, etc.).

Probes can be made from a variety of materials such including ceramics, metals, plastics, and even wood. Although probes have been described that basically have rod-like shapes, other probe shapes (including curved rod shapes) are possible. Probes can also be designed to be flexible, as was mentioned earlier.

Several of the collimation methods which can be used to enhance acoustic, optic, photo-acoustic, and acousto-optical imaging of concealed objects in an obscuring medium can be implemented in an imaging system which employs ionizing radiation. It is desirable to control radiation beam properties such as pulse shape, repetition rate, coherence length, coding, its angular distribution, its frequency distribution, and its spatial distribution (in one-, two-, and three-dimensions). In addition, properties such as phase (using a pulsed or modulated source) and polarization can also be exploited for both electromagnetic and neutron ionizing radiation (although limitations imposed by energy dependence need to be considered in practice). The ability to control some or all of these beam properties can be useful in determining the location and material characteristics of the obscured object. Thus, collimation methods such as gaps, mechanical apertures (slits, slots, holes), grids, fibers, masks, coded or patterned apertures, focusing lens, polarizing filters, diffractive spatial filters, narrow spectral bandwidth and directionally-sensitive filters such as crystals and multilayer mirrors, waveguides (capillary optics, periodic layers, microchannel plates, etc.), time-resolved techniques such as gating (electronic collimation of the detector) used in TOF measurements, coupling materials, reciprocating collimators (including grids and waveguides), etc., can be employed when appropriate. These collimation techniques allow us to modify and improve current systems which use ionizing radiation to image concealed objects in an obscuring medium.

Consider a conventional mine detection system that uses a radioisotope source (electromagnetic ionizing radiation or neutrons). Substantial collimation from mechanical apertures (holes, slits, slots) and radiation shielding can be employed in an effort to create a radiation beam with some degree of directionality. The radioisotope source provides narrow bandwidth radiation. Much of the radiation emitted is wasted since the radioisotope acts as an omnidirectional source. The radioisotope is also self-attenuating which limits the amount of material that can be used and can result in the material being shaped into more efficient geometries. The choice of radiation energy(s) is quite limited. The use of accelerators such as conventional x-ray tube sources or spallation neutron generators as alternatives to radioisotope sources may not be viable if only mechanical apertures and absorptive filters are available. These man-made sources are (typically) not highly directional and do not have a narrow bandwidth. A subset of the backward scattered radiation is measured by a collimated detector using a mechanical aperture (a slit, slot, hole) or grid. By re-orienting the collimation, it is possible to make measurements of the scatter distribution (while excluding most of the radiation which is single-backscattered). Changes in the backscatter levels or distribution may indicate the presence of an object such as a mine. Scatter field measurements can also be made at positions that are off-set from the location of the incident beam (a technique we have previously used for optical imaging in tissue). The radiation detector (gas, liquid, scintillator, semiconductor) usually offers energy resolution and can be electronically collimated (gated). Thus, the detector with a collimator can offer limited angular resolution and energy discrimination. Detector maintenance (including calibration), initial cost, and replacement cost (in addition to extensive shielding and the presence of a substantial amount of an always-active radioisotope) can limit the use of this type of system in practice.

The radioisotope-based imaging system design can be improved by employing waveguides (such as hollow core fibers, capillary optics and structured collimators, or periodic layers) and narrow spectral bandwidth and directionally-sensitive filters such as multilayer mirrors, diffractive powders, or crystals as collimators. The use of one or both of these types of collimators can enhance the present design or permit the design to be substantially modified. Versions of the waveguide (microchannel plates, capillary waveguides, capillary optics, periodic layers) have been used for neutrons and x-rays. See W. Vefterling, et al., Measurements on an X-Ray Light Pipe at 5.9 and 14.4 KeV, J. Opt. Soc. Am., Vol. 66, No. 10, p.1048–1049, (1976); V. Arkadlev, et al., Transport of X-Rays Along Capillary X-Ray Waveguides Under Conditions of Total External Reflections from Curved Surfaces, Phys. Chem. Mech. Surfaces, Vol. 6(1), pp. 82–91 (1990); S. Wilkins, et al., On the Concentration, Focusing, and Collimation of X-Rays and Neutrons Using Microchannel Plates and Configurations of Holes, Rev. Sci. Instrum., Vol. 60(6), pp.1026–1036 (1989); and V. Arkadlev, et al., Wide-Band X-Ray Optics with a Large Angular Aperture, Sov. Phys. Usp., Vol. 32(3), pp.271–276 (1989). The versions will be collectively referred to as capillary optics here. They offer a degree of angular selectivity and energy selectivity.

The narrow spectral bandwidth and directionally-sensitive filter is a multilayer mirror(s) or a Bragg (including mosaic) crystal(s) (see Nelson, et. al. U.S. Pat. No. 4,958,368 (Sep. 18, 1990, U.S. Pat. No. 4,969,175 (Nov. 6, 1990)) which have been used for neutrons and x-rays (including polarized neutrons and x-rays). Both Bragg crystals and multilayer mirrors will be referred to as multilayer mirrors. In many instances capillary optics offer the potential of collimating (focusing) radiation (at the source or receiver) at a lower cost than with curved multilayer mirrors. The ability to focus ionizing radiation for imaging purposes offers a further advantage if the object can be incapacitated in an acceptable period of time by a sufficient dose of radiation. Multilayer mirrors offer the potential of a selectable energy (and in some cases polarization) with moderate-to-very high energy resolution over a small angular range. More than one multilayer mirror can be used to collimate the source beam and the mirrors can be of different design to further refine the beam spectrum. Thus, an uncollimated narrow or broad energy bandwidth source (for example, a x-ray tube typically provides a broad bandwidth spectrum) can be converted into a collimated narrow bandwidth energy source with acceptable efficiency. The directional and spectral properties of the source beam will be well-controlled.

The use of capillary optics can enhance the utilization efficiency of source radiation and can permit the source distribution to be altered (use an extended source or a shaped source) in much the same manner as a mechanical structured collimator used with a multilayer mirror would (see Nelson, et. al., U.S. Pat. No. 4,958,368 (Sep. 18, 1990) and U.S. Pat. No. 4,969,175 (Nov. 6, 1990)). Just as a mechanical structured (patterned) collimator can undergo reciprocating motion to smooth out the image of its own pattern so too can capillary optics. Multilayer mirrors and/or capillary optics can also be used to collimate and filter desirable scattered radiation prior to reaching the detector (Compton scatter imaging and material composition identification techniques have been used in radiology and non-destructive testing).

This approach (imaging with a radiation beam which originates inside the medium and is comprised of scatter radiation) is comparable to the virtual collimated beam concept we have used with acoustic and optical radiation. If the incident radiation beam induces an effect such as fluorescence, then the fluorescence radiation can be imaged if it is able to escape from the medium. As was mentioned previously, the use of multiple angled beams, reference objects, and reference images (and guide stars) can also be used to enhance image information acquired with ionizing radiation.

Figure 7:
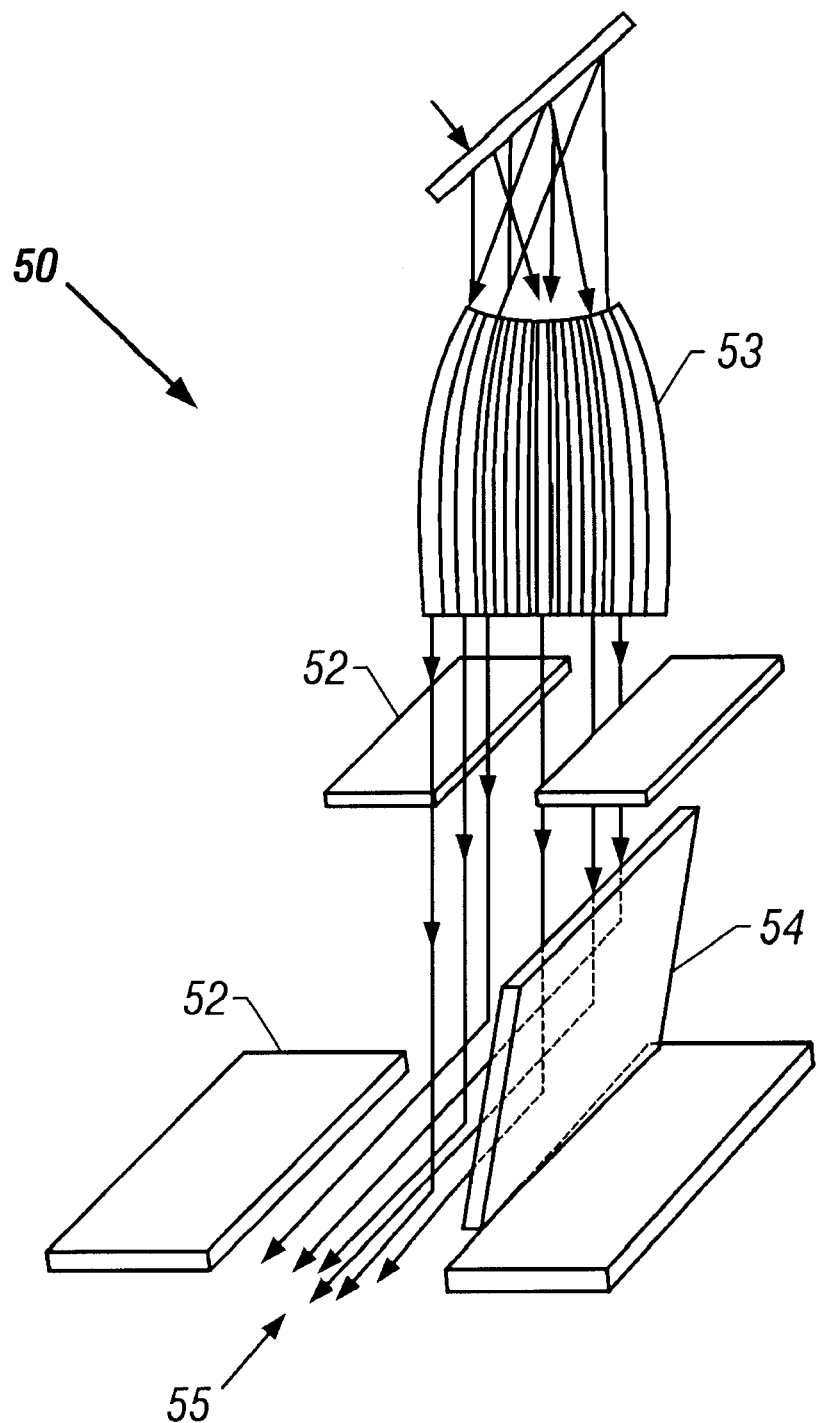
FIG. 7 shows a system 50 having an extended ionizing radiation source 51 which uses mechanical apertures (e.g., slits) 52, a capillary optics focusing lens 53, and a multilayer mirror 54 to produce a narrow bandwidth, directional, collimated beam 55.
Figure 8:
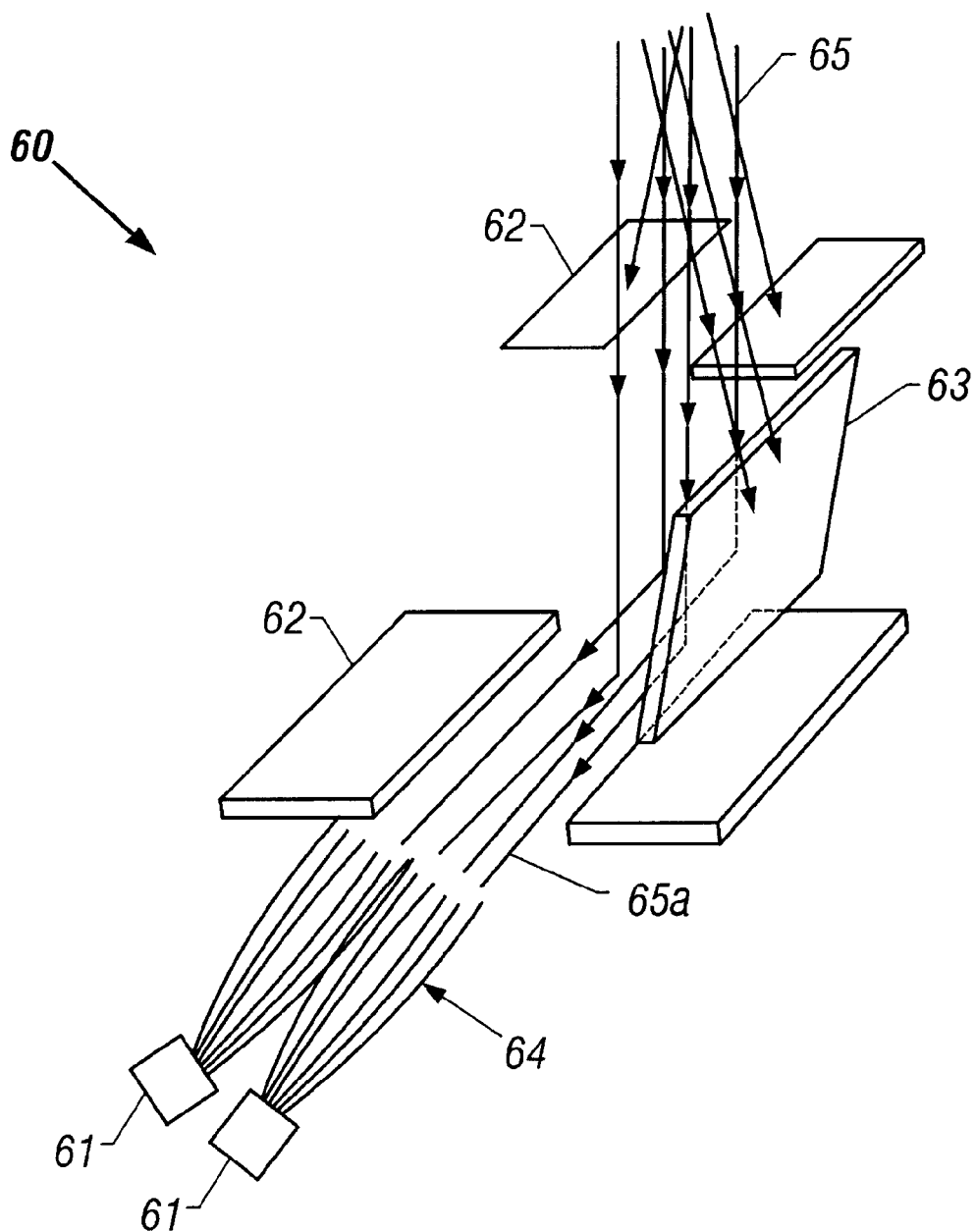
FIG. 8 shows a system 60 having a receiver comprised of two radiation detectors 61 with collimation provided, for example, by mechanical apertures (slits) 62, a multilayer mirror 63, and a capillary optics focusing lens 64. The capillary optics lens 64 is preferably configured with a split output so that ionizing radiation 65/65*a* leaving the medium is directed to the detectors 61.
Figure 9:
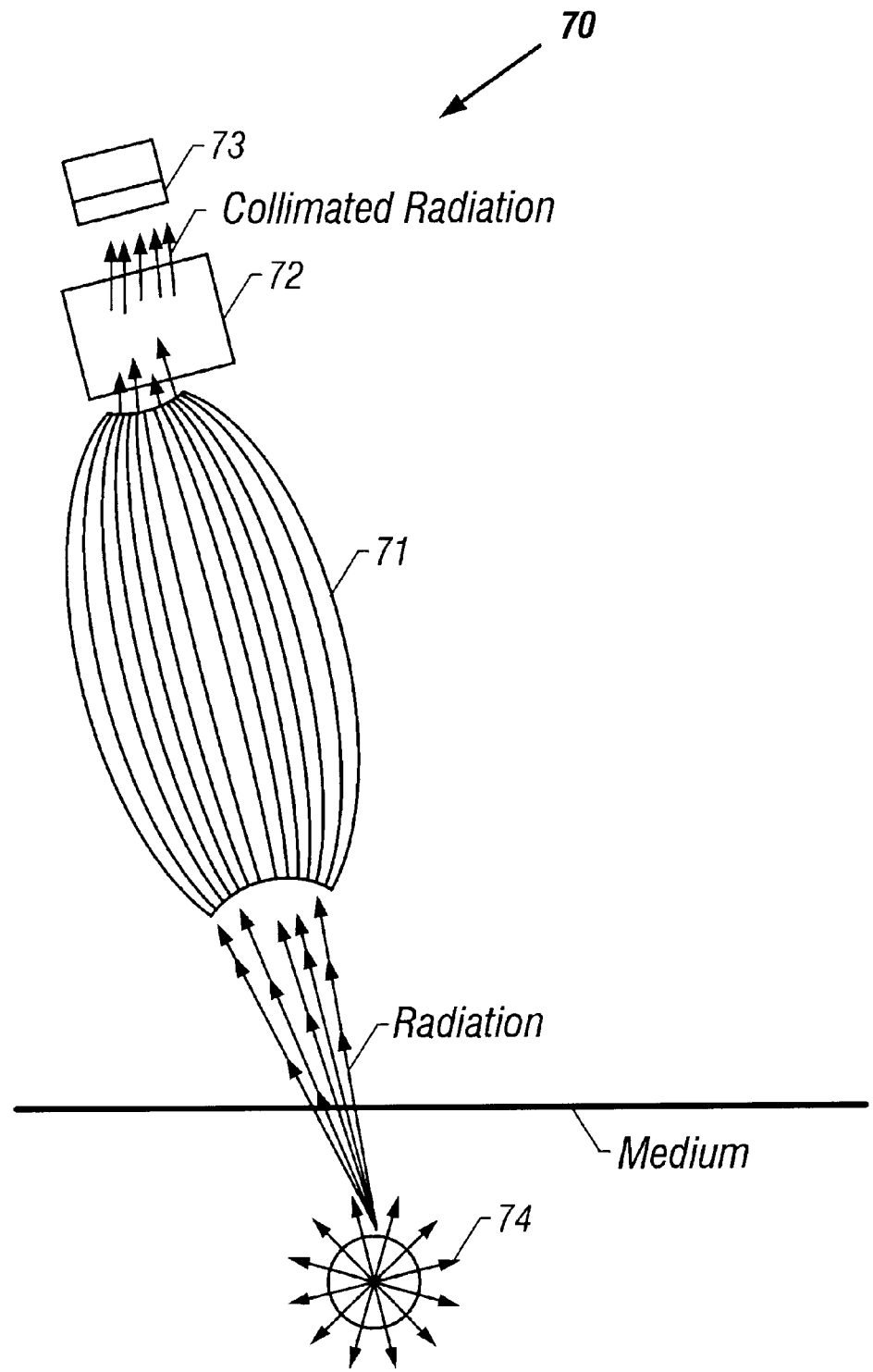
FIG. 9 shows a system 70 having a receiver comprised of a focused, full capillary optics lens 71, a multilayer mirror 72, and a radiation detector 73. The lens 71 (which preferably can be scanned vertically and horizontally, and tilted) is shown focused at the depth of an object 74. Additional mechanical apertures (not shown) can be employed if needed.
Figure 10A:
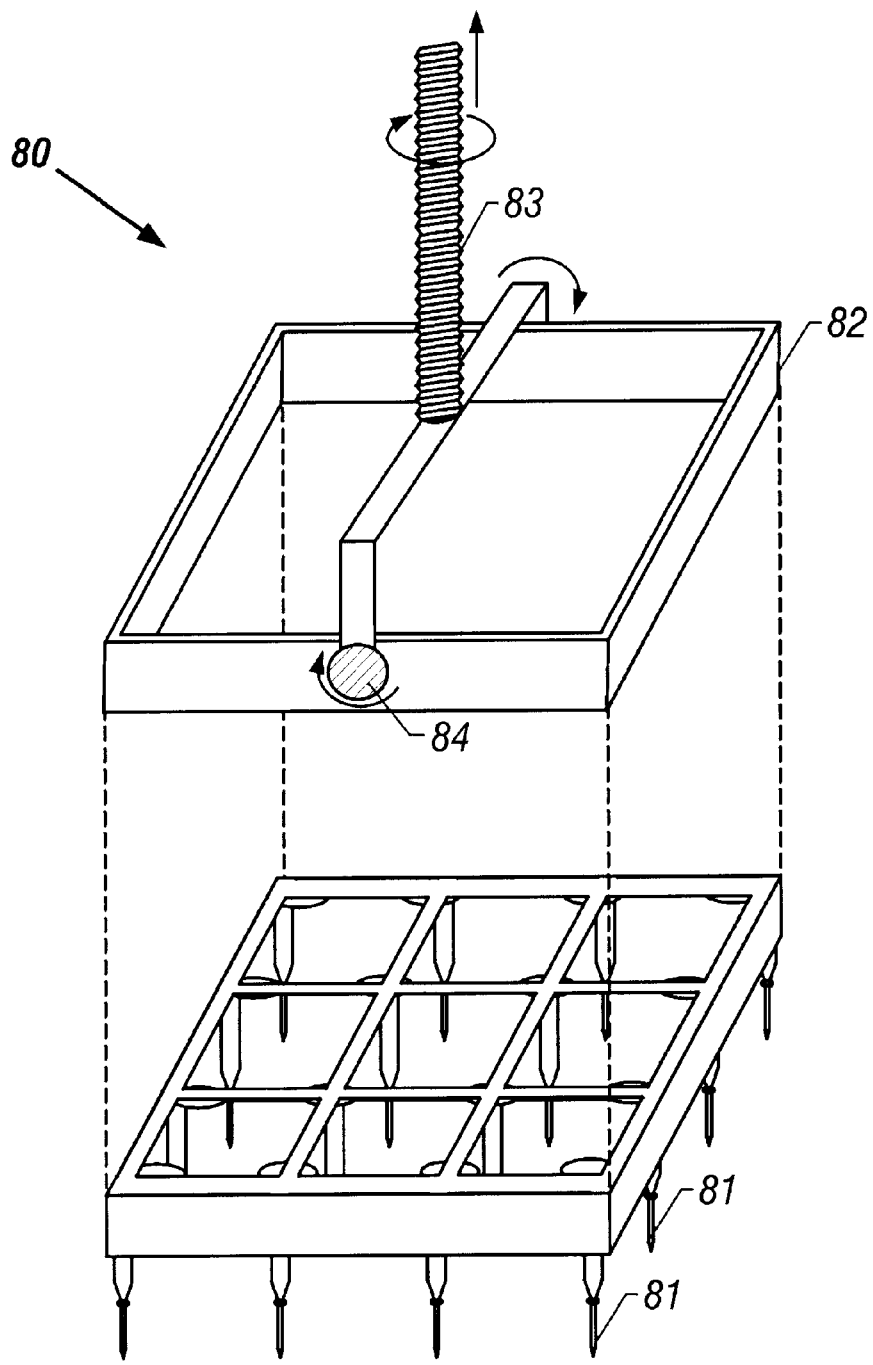
FIG. 10*a* shows a probe module 80 comprised of an array of sixteen probes 81. Power, electronic controls, and readout connections to the probes 81 and optional probe orientation motors are not shown. The probe module 80 can be placed in a mounting platform 82 which can be elevated or lowered using a drive shaft 83. The mounting platform 82 can be rotated about the axis of the drive shaft 83. Platform orientation motors 84 can be used to change the orientation angle of the mounting platform 82 with respect to the axis of the drive shaft 83 (and thus the surface of the medium (not shown)). A simple variation on this design incorporates the probe module 80 and the mounting platform 82 into a single unit. Although probes 81 are shown in a rectangular array formation, other uniform and non-uniform array configurations can be implemented. The number of probes 81 and spacings between probes 81 can be optimized for a specific imaging problem. Versions of the probe module 80 design can be hand-held, mounted on a frame with wheels which can be pushed, or mounted on a vehicle in a manner similar to the rotating brush design shown in FIG. 6.
Figure 10B:
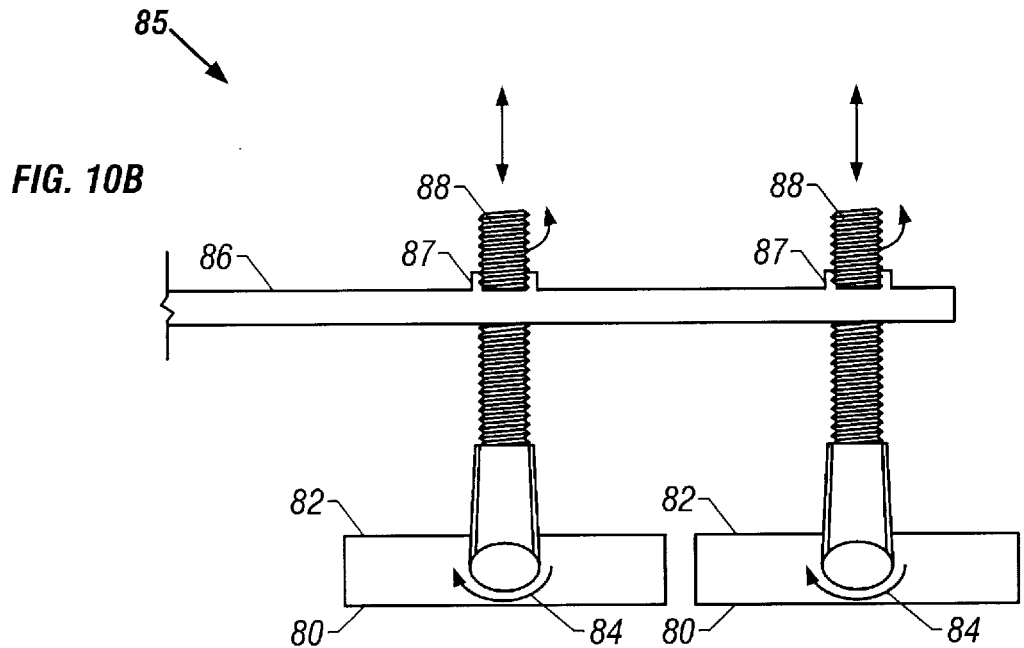
FIGS. 10*b* and 10*c* show, from front and top perspectives respectively, a dual probe module system 85 (comprising dual probe modules 80 on mounting platforms 82) mounted on a support arm 86 which preferably has independent drive shaft motors 87 which can be used to raise and lower the probe module mounting platforms 82 and rotate the mounting platforms 82 about the axis of their respective drive shafts 88. The support arm 86 preferably can be attached to a moveable platform (not shown) for purposes of scanning a large surface area. Although platform orientation motors 84 are shown as part of the probe module mounting platforms 82, this additional degree of freedom can be incorporated into the mounting platform support arm 87. The support arm 87 can be designed to hold one, two, or more mounting platforms 82 and an imaging system can include more than one support arm 87.
Figure 10C:
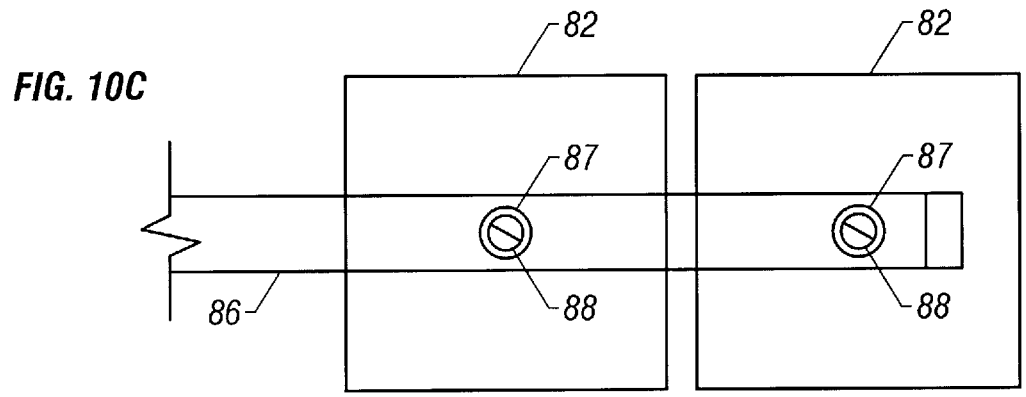
Figure 10D:
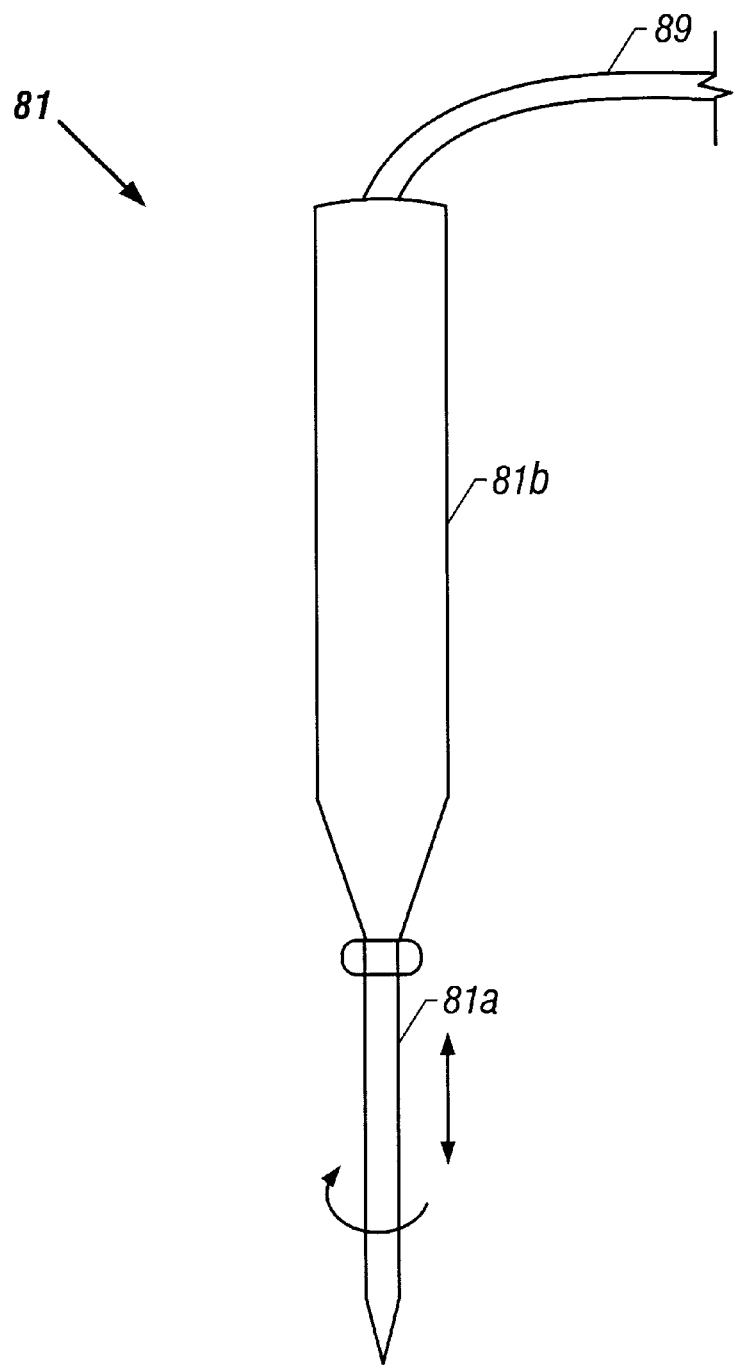
FIG. 10*d* shows a simple mechanical probe 81 with a probe shaft 81*a* and body 81*b* (which preferably contains a drive unit (not shown) that can be used to raise or lower the probe shaft 81*a* and optionally cause the shaft 81*a* to rotate). The probe body 81*b* also preferably contains a pressure sensor (not shown) and can preferably contain a clutch (not shown) if rotation is possible, both of which are preferably coupled to the shaft 81*a*. Alternatively, pressure sensors and clutches (if needed) can be located external to the probe body (as is done in many boring devices or systems which use hydraulics. Power, electronic control, and readout connections are provided through cable 89, thereby permitting each probe 81 to function independently of other similar probes.

FIG. 7 shows a radiation source configuration consisting of an extended radiation source coupled to a capillary optics collimator (half of a capillary lens unit) and a multilayer mirror collimator. The capillary optics will reduce the energy bandwidth of the original source while focusing a fraction of the divergent source radiation toward the multilayer mirror. The energy distribution and angular distribution of this directional beam are next filtered by a multilayer mirror, resulting in a narrow bandwidth, highly directional radiation beam. The use of capillary optics to efficiently collect (or redirect) radiation simplifies the geometric design requirements for the multilayer mirror. For example, it might be difficult to design and manufacture a highly focused multilayer mirror for use at diagnostic x-ray energies. If an imaging application requires the use of a full capillary lens unit with one or more collimated outputs (see FIG. 8), then the size of the multilayer mirror(s) can be reduced. It is also possible to implement a hybrid source lens which consists of the capillary lens and mirror of FIG. 7 followed by the capillary lens of FIG. 8 (lens-filter-lens system). This design results in an energy-selectable, narrow bandwidth, focused source. An alternative arrangement is to combine both lens halves into a single focused lens system followed by a mirror. A single focused lens is shown in FIG. 9. FIG. 8 shows a radiation receiver configuration which uses a multilayer mirror collimator and a capillary optics collimator. In this case the multilayer mirror provides scatter rejection with respect to the direction and energy of the desired scattered radiation. This means a less-expensive detector (with lower energy resolution) might be used or that the energy resolution of the detector will improve due to the reduced count rate resulting from the filtering of undesirable radiation.

The source and receiver configurations can be used separately or together as part of an imaging system. For example, if the source is a radioisotope and a sufficiently intense and directional radiation beam can be produced by using a mechanical aperture (slit, slot, hole) or grid as collimation, then source capillary optics and/or multilayer mirror collimation may not be needed. Similarly, imaging applications may occur where a significant benefit is derived by using a directional and narrow bandwidth source beam (produced using capillary optics and a multilayer mirror or simply capillary optics if the source, such as an isotope, inherently has a narrow bandwidth) with a well-defined cross section while the detector only requires sufficient mechanical collimation (or a grid) and/or an air gap. For example, a gamma camera (used in Nuclear Medicine) or similar device with a focused collimator can offer sufficient energy resolution and angular resolution so as to perform adequately for transmission or scatter imaging tasks (such as mine detection). If an imaging system uses both source and receiver capillary optics, then it is desirable to reduce alignment problems between these two capillary collimators. In some applications the receiver capillary optics might be eliminated if they introduce alignment difficulties or provide little benefit relative to the additional cost.

FIG. 8 shows a focused capillary optics lens concentrating radiation to two separate radiation detectors, further reducing the cost of the detectors. A similar lens design can be used with two separate sources (in place of a large extended source) rather than two separate receivers. The concept can be extended to create arrays of discrete sources and/or receivers from a single capillary lens or by abutting or joining multiple, small capillary lenses. The source and receiver configurations can be used together to image the desired exiting radiation. Types of exiting radiation which might be imaged include transmitted radiation (which has undergone little or no scattering), scattered radiation (forward and backward), virtual collimated scattered beam radiation, and fluorescence or conversion (the result of nuclear interactions) radiation. In some imaging problems it may be more cost-effective to use the multilayer mirror between the detector and the capillary optics rather than the capillary optics between the multilayer mirror and the detector (as is shown in FIG. 8).

Multiple-angle data acquisition can be implemented permitting the use of transmission or scatter tomosynthesis reconstruction techniques and material composition analysis. If a sufficiently large range of viewing angle image data can be acquired, then CT reconstruction can be implemented. Images can be acquired using multiple energies, permitting the use of image enhancement techniques (such as dual energy subtract, etc.) already developed for use in diagnostic radiology and non-destructive testing. Polarization-dependent effects can also be measured. In addition, coupling materials can be employed if needed as we have described in the cases of imaging with acoustic, electromagnetic (optical), and photo-acoustic radiation. Coupling materials can be used for purposes such as to provide a more-uniform interface (or medium) or reduce index mismatches. Contrast and agent materials can also be used as was described previously (including promoting changes in temperature). The coupling, contrast, or agent material can be delivered from a module or probe or an independent unit such as a sprayer, hose, etc. (In other applications contrasts or agent materials might be injected into the medium, introduced into a pipe, etc.) In addition, induced changes in medium or object properties (for example, as the result of temperature changes or acoustic radiation) can be evaluated using ionizing radiation in a manner similar to optical radiation (for example, the acousto-optic effect). The receiver configuration (with or without capillary optics) can be used to image radioisotope sources within or near the concealed object in the obscuring medium.

Just as a half (FIG. 7) or full capillary lens can be used to focus a radiation source so too a half or a full capillary lens can be used to focus emission, fluorescence or scattered radiation from a localized region within the medium to a detector. A multilayer mirror can be included to provide additional filtration if needed (see FIG. 9). The depth at which the lens is focused can be adjusted by tilting the lens or elevating or lowering the lens with respect to the surface of the medium since the lens is likely to have a fixed focus length. This is similar to the optical and acoustic techniques using a focused lens which we have described previously. (A system with a variable focus is much easier to implement in optics). The lens can also be scanned in a geometric pattern to provide additional image information. Focused collimators (typically made from materials such as tungsten or lead) have been used for many years to image radioisotope emissions in Nuclear Medicine. Focused collimators such as focused x-ray grids are widely used in x-ray radiography. A number of factors influence the cost-effectiveness of using capillary optics and multilayer mirrors in place of conventional collimators and materials which act as energy filters. The source strength, collimation and energy distribution; the scattering and absorptive properties of the concealed object and the obscuring medium; the detector size, energy resolution, and efficiency can affect how and when capillary optics and multilayer mirrors should be integrated into the design of an imaging system.

The source and/or receiver configurations just described which use multilayer mirrors and/or capillary optics can be readily adapted for use in transmission and scatter imaging in diagnostic radiology. The advantages of improved efficiency of use of source radiation, a selectable energy, a narrow energy bandwidth, and a collimated beam (which can improve scatter rejection capability and may permit a reduction in detector size) can all be used to improve image quality. Applications such as mammography, dual-energy subtraction, multiple energy imaging, Compton imaging, imaging of contrast material, imaging of fluorescence, the detection of osteoporosis, CT, tomosynthesis, the imaging of radioisotopes, etc. can benefit from this approach to imaging system design. The use of source capillary optics with multilayer mirrors and receiver capillary optics with or without multilayer mirrors may depend on factors such as alignment problems, cost of capillary optic units and multilayer mirrors, and the cost of detectors. Thus, in a mammography imaging system with a film-screen detector (large area, limited energy resolution, limited dynamic range), compression plates (typically, but not always, employed), a slit or slot scan arrangement, and a source configuration which uses capillary optics and a multilayer mirror, the use of receiver capillary optics may be of limited benefit in enhancing the image information content relative to the added cost. Indeed, if the exiting radiation beam spectrum and scatter content level are acceptable, then an air gap or an air gap with x-ray grid (or mechanical aperture) may provide satisfactory collimation, and the use of a multilayer mirror between the tissue and the detector would not be cost-effective. (This conclusion may also be applicable for other radiographic applications such as CT, imaging of contrast material, tomosynthesis, etc.). Both a grid and a multilayer mirror will result in a loss of primary radiation (in transmission mammography) and additional energy filtering would reduce the scatter levels at the detector by a small amount (assuming an average breast thickness and the use of compression plates).

On the other hand, if small CCD (coupled to x-ray phosphor) detector arrays (good dynamic range) or small semiconductor detector arrays (good dynamic range, moderate or good energy resolution) were to be used (see Nelson U.S. Pat. No. 4,937,453 (Jun. 26, 1990) and U.S. Pat. No. 5,017,782 (Nov. 19, 1990)), the relative benefit of focusing the transmitted radiation is much greater. The source configuration would benefit from the use of focused capillary optics which will improve the efficiency of use of source radiation. Capillary optics can be readily incorporated into medical imaging system designs which use multilayer mirrors (See Nelson, et. al., U.S. Pat. No. 4,958,368 (Sep. 18, 1990) and U.S. Pat. No. 4,969,175 (Nov. 6, 1990)).

An additional benefit of using small detectors in an application such as mammography is the ability to use smaller compression plates or smaller shaped compression plates (if advantageous). These plates can have open regions which can eliminate the effects of plate material in the beam path and permit the use of new compositions of plate materials. Greater compression is possible (relative to conventional large plates) and edge effects (at surfaces that are not in contact with the plates) due to variations in tissue thickness with position can be reduced. A conventional compression plate pair is separated by a (approximately) 5 cm gap when used with a typical breast in x-ray mammography. Non-uniform tissue thickness is encountered for those remote parts of the breast surface not in contact with the plates (for example, the nipple). A smaller compression plate design should permit greater compression (and a smaller gap) for these remote parts of the breast surface, reducing the need for elaborate compensating measures.

Electronic methods to compensate for variations in attenuation and scatter due to variations in tissue thickness can involve corrective signal processing filters which are weighted by the geometry of the tissue thickness variations. The geometry can be estimated by a number of methods, including the transmission measurements, acoustically, a profile recorded with an electronic camera, etc. In addition, the small compression plates permit a number of discrete compression measurements to be acquired where the plate separation is varied. Thus, many techniques can be employed independently or combined to formulate a calibration or correction filter for the case of imaging which involves non-uniform tissue thickness (the same concepts apply to mediums other than tissue). Scatter content can also be measured to further refine the corrections (as we have described in previous patents for optical imaging of tissue). Estimates for the effects of variations of tissue thickness (and the effect of a discontinuous medium (tissue in contact with air)) can also be applied to the edge effect problem in optical and acoustical mammography (although we have discussed an alternative, an optical or acoustical coupling material to fill the gaps, in earlier patents). As in the case for ionizing radiation, similar calibration filters can also be developed. The benefit of a smaller compression plate in optical and acoustic mammography has been described in previous patents.

Although the invention has been described with respect to specific preferred embodiments thereof, many variations and modifications will immediately become apparent to those skilled in the art. It is, therefore, the intention that the appended claims be interpreted as broadly as possible in view of the prior art to include all such variations and modifications.

We claim:

1. An apparatus for obtaining images of concealed objects in an obscuring medium comprising:
    at least one radiation source providing acoustic radiation, the at least one source disposed so radiation therefrom will be incident on an obscuring medium to be scanned,
    at least one radiation detector associated with the at least one radiation source and disposed to detect radiation exiting the medium,
    a collimator associated with each detector and disposed between the medium and each detector, wherein the obscuring medium is at least one of snow, ice, gravel, sand, soil, mud, river bottom, lake bottom, ocean bottom, biological waste, sewage or sludge, and human tissue, and
    a radiation-transparent module having an elastically conformable contact surface, wherein the contact surface is free of rigid support members and is conformable to a discontinuous or irregular medium surface, wherein the module is positioned between at least one of the following two pairs: the radiation source and a radiation entrance surface of the medium, and a radiation exit surface of the medium and the radiation detector, the module providing a uniform entry surface profile for the radiation incident on the obscuring medium.

2. The apparatus of claim 1 further comprising a radiation coupling material disposed between at least one of the following two parts: the radiation-transparent module and the radiation entrance surface of the medium, and the radiation exit surface of the medium and the radiation-transparent module.

3. The apparatus of claim 2 wherein the coupling material feely conducts acoustic radiation.

4. The apparatus of claim 3 wherein the coupling material provides at least one of a contrast material and an agent material.

5. The apparatus of claim 1 further comprising a collimator associated with each source and disposed between the source and the medium.

6. The apparatus of claim 1 wherein the collimator comprises at least one of an air gap, an electronic collimator, a gap, a mechanical aperture, a focused lens, a waveguide, a phased array, a directionally-sensitive filter, a spectrally-sensitive filter, a directionally-sensitive and spectrally-sensitive filter, an acousto-optical device which exhibits high angular selectivity, a coupling material, and a source-detector system which implements at least one of a time-resolved and a diffusive wave technique.

7. The apparatus of claim 1 wherein the at least one source provides at least one of a coded waveform, a complex waveform, a modulated waveform, a continuous waveform, and a pulsed waveform.

8. The apparatus of claim 1 wherein the at least one detector comprises an acoustical radiation detector.

9. The apparatus of claim 8 wherein the at least one acoustical radiation detector comprises at least one of a deformable mirrored deflection plate, a reflective elastic layer, and a transducer.

10. The apparatus of claim 1 wherein at least one source of radiation is disposed so radiation from the source is incident over a plurality of angles on the medium to be scanned.

11. The apparatus of claim 10 wherein the medium is human tissue.

12. The apparatus of claim 1 further comprising at least one additional radiation detector disposed to detect radiation exiting the medium, and at least one additional collimator associated with the at least one additional detector, the at least one additional collimator disposed between the medium and the at least one additional detector.

13. The apparatus of claim 12 wherein the at least one additional radiation detector and associated at least one additional collimator are disposed to measure at least one of transmitted radiation, backscattered radiation, scatter contribution in transmitted radiation, scatter contribution in backscattered radiation, virtual collimated transmitted radiation, virtual collimated backscattered radiation, radiation due to energy conversion, radiation due to a resonance condition, radiation due to the physical structure of the object, radiation due to Doppler scattering, diffuse radiation, speckle, and holographic interferometry patterns.

14. The apparatus of claim 1 wherein at least one radiation detector is disposed to detect at least one of transmitted radiation, backscattered radiation, scatter contribution in transmitted radiation, scatter contribution in backscattered radiation, virtual collimated transmitted radiation, virtual collimated backscattered radiation, radiation due to energy conversion, radiation due to a resonance condition, radiation due to the physical structure of the object; radiation due to Doppler scattering, diffuse radiation, speckle, and holographic interferometry patterns.

15. The apparatus of claim 1 wherein at least one radiation source is at least one of an acoustic radiation source and at least one detector corresponds to the at least one acoustic radiation source, and the at least one detector comprises at least one of a deformable mirrored deflection plate, a reflective elastic layer, and a transducer.

16. The apparatus of claim 1 further comprising a delivery system to deliver at least one of a contrast material and a contrast agent to the medium.

17. The apparatus of claim 1 further comprising at least one of a detection system, a rotating brush, an air jet, and a water jet, wherein the detection system is configured to perform at least one of the functions of determining the roughness and irregularities of a surface of the medium and locating objects on the surface of the medium, and wherein the rotating brush, air jet, and water jet are configured to clear debris, reduce surface roughness and irregularities, and to uncover objects in the medium.

18. The apparatus of claim 17 including a deployable bolt configured to penetrate the obscuring medium and contact an object concealed in the medium.

19. An apparatus for obtaining images of concealed objects in an obscuring medium comprising:

at least one acoustic radiation source disposed so radiation therefrom will be incident on an obscuring medium to be scanned, and at least one radiation detector comprising a bladder positioned adjacent the medium, the bladder including an elastic contact surface free of any rigid support members and configured to be coupled to the medium to provide a uniform entry and exit surface for the radiation incident on the obscuring medium to be scanned, wherein the bladder is further configured to detect radiation exiting from the at least one radiation source.

20. The apparatus of claim 19 wherein the at least one acoustic radiation source comprises at least one acoustic transducer.

21. The apparatus of claim 20 wherein the at least one acoustic transducer is a source of acoustic radiation and a receiver of acoustic radiation.

22. The apparatus of claim 19 wherein the bladder includes at least one of a deformable mirrored deflection plate and a reflective elastic layer.

23. A method for obtaining images of concealed objects in an obscuring medium, wherein the medium is at least one of snow, ice, gravel, sand, soil, mud, river bottom, lake bottom, ocean bottom, biological waste, sewage or sludge, the method comprising the steps of:

(1) positioning a radiation-transparent module having an elastically conformable contact surface free of rigid support members proximate a medium to be scanned, wherein the elastically conformable contact surface is conformable to a discontinuous or irregular medium surface and provides a uniform entry surface profile for the radiation incident on the obscuring medium, (2) irradiating a volume of the medium with acoustic radiation, (3) collimating radiation exiting the medium, and (4) detecting at least one of transmitted radiation, backscattered radiation, scatter contribution in transmitted radiation, scatter contribution in backscattered radiation, virtual collimated transmitted radiation, virtue collimated backscattered radiation, radiation due to energy conversion, radiation due to a resonance condition, radiation due to the physical structure of the object, radiation due to Doppler scattering, diffuse radiation, speckle interferometry patterns, and holographic interferometry patterns.

24. The method of claim 23 comprising the additional step of:

(5) introducing a coupling material between the elastically conformable contact surface and the medium prior to irradiating the volume of medium.

25. The method of claim 23 comprising the additional steps of:

(5) repeating steps (2)–(4) with the radiation source rotated, (6) repeating step (5), and (7) using at least one of tomosynthesis techniques or computed tomography techniques to reconstruct an image.

* * * * *

UNITED STATES PATENT AND TRADEMARK OFFICE
CERTIFICATE OF CORRECTION

PATENT NO.   : 6,216,540 B1
DATED        : April 17, 2001
INVENTOR(S)  : Nelson et al.

It is certified that error appears in the above-identified patent and that said Letters Patent is hereby corrected as shown below:

Column 24,
Line 1, please delete "ago".

Column 26,
Line 7, please change "aecontrast" to -- contrast --.

Column 33,
Lines 9-10, please change "ferroagnetic" to -- ferromagnetic --.
Line 10, please change "arameters" to -- parameters --.

Signed and Sealed this

Twenty-third Day of April, 2002

Attest:

JAMES E. ROGAN
*Director of the United States Patent and Trademark Office*

*Attesting Officer*